US012605376B2

(12) United States Patent
Garren et al.

(10) Patent No.: US 12,605,376 B2
(45) Date of Patent: Apr. 21, 2026

(54) METHODS OF TREATING RELAPSING MULTIPLE SCLEROSIS USING AN INHIBITOR OF BRUTON'S TYROSINE KINASE

(71) Applicants: Genentech, Inc., South San Francisco, CA (US); Hoffmann-La Roche Inc., Little Falls (CA)

(72) Inventors: Hideki Garren, Palo Alto, CA (US); Edmond Huatung Teng, San Mateo, CA (US); Aurelien Viaccoz, Basel (CH); Hans-Christian Von Buedingen, Basel (CH)

(73) Assignees: Genentech, Inc., South San Francisco, CA (US); Hoffmann-La Roche Inc., Little Falls, NJ (US)

( * ) Notice: Subject to any disclaimer, the term of this patent is extended or adjusted under 35 U.S.C. 154(b) by 642 days.

(21) Appl. No.: 17/995,259

(22) PCT Filed: Apr. 1, 2021

(86) PCT No.: PCT/US2021/025301

§ 371 (c)(1), (2) Date: Sep. 30, 2022

(87) PCT Pub. No.: WO2021/202825

PCT Pub. Date: Oct. 7, 2021

(65) Prior Publication Data

US 2023/0149395 A1 May 18, 2023

Related U.S. Application Data

(60) Provisional application No. 63/051,767, filed on Jul. 14, 2020, provisional application No. 63/005,095, filed on Apr. 3, 2020.

(51) Int. Cl.

| | |
|---|---|
| *A61K 31/4985* | (2006.01) |
| *A61P 25/00* | (2006.01) |
| *A61P 37/00* | (2006.01) |

(52) U.S. Cl.

CPC .......... *A61K 31/4985* (2013.01); *A61P 25/00* (2018.01); *A61P 37/00* (2018.01)

(58) Field of Classification Search

CPC ....... A61K 31/4985; A61P 37/00; A61P 25/00

See application file for complete search history.

(56) References Cited

U.S. PATENT DOCUMENTS

| | | | |
|---|---|---|---|
| 8,716,274 | B2 | 5/2014 | Crawford et al. |
| 8,921,353 | B2 | 12/2014 | Crawford et al. |
| 9,238,655 | B2 | 1/2016 | Crawford et al. |
| 9,782,405 | B2 | 10/2017 | Crawford et al. |
| 10,045,983 | B2 | 8/2018 | Crawford et al. |
| RE48,239 | E | 10/2020 | Crawford et al. |
| 2016/0038496 | A1 | 2/2016 | Shu et al. |
| 2019/0194203 | A1 | 6/2019 | Crawford et al. |
| 2020/0062769 | A1 | 2/2020 | Crawford et al. |
| 2021/0079002 | A1 | 3/2021 | Crawford et al. |
| 2023/0091561 | A1 | 3/2023 | Garren et al. |

FOREIGN PATENT DOCUMENTS

| | | | | |
|---|---|---|---|---|
| CN | 107043366 A | 8/2017 | | |
| EP | 3626239 A1 | 3/2020 | | |
| WO | 2013/067274 A1 | 5/2013 | | |
| WO | WO-2019208805 A1 * | 10/2019 | ........... A61K 31/496 | |
| WO | WO-2020055698 A1 * | 3/2020 | ......... A61K 31/4545 | |
| WO | 2020/154252 A1 | 7/2020 | | |
| WO | 2021/173740 A1 | 9/2021 | | |

OTHER PUBLICATIONS

Anderson, D.W., et al., "Revised estimate of the prevalence of multiple sclerosis in the United States" Ann Neurol 31(3):333-336 (Mar. 1, 1992).

Bruton, O., et al., "Agammaglobulinemia" Pediatrics 9(6):722-728 (Jun. 1, 1952).

Cohen, S., et al., "Fenebrutinib Compared to Placebo and Adalimumab in Patients with Inadequate Response to Either Methotrexate Therapy or Prior TNF Therapy: Phase 2 Study" Abstract (OP0025; Annual of Rheumatic Diseases, vol. 78:Issue Suppl. 2) Annual European Congress of Rheumatology, Eular 2019, Madrid, Spain, pp. A80 (1-2) ( Jun. 12-15, 2019).

Conley, M.E., et al., "Genetic analysis of patients with defects in early B-cell development" Immuno Rev 203(1):216-234 (Feb. 1, 2005).

Crawford, J., et al., "Discovery of GDC-0853: A Potent, Selective, and Noncovalent Bruton's Tyrosine Kinase Inhibitor in Early Clinical Development" J Med Chem 61(6):2227-2245 (Mar. 22, 2018).

Cree, B.A.C., et al., "Silent progression in disease activity-free relapsing multiple sclerosis" Ann Oncology 85(5):653-666 (May 1, 2019).

Dolgin, E., et al., "BTK blockers make headway in multiple sclerosis" Nat Biotechnol News 39(1):1-3 (Jan. 1, 2021).

Greenberg, B., and Traboulsee, A., "Bruton Tyrosine Kinase Inhibitors for MS—Progress in the Development of an Emerging Therapeutic Approach" Slides and Program Book Excerpt; Annual Meeting of the Consortium of Multiple Sclerosis Centers, Orlando, FL, USA, pp. 1-57 (Oct. 27, 2021).

Gregson, A., et al., "Emerging small-molecule treatments for multiple sclerosis: focus on B cells" F1000 RES 8(F1000 Faculty Rev):245 (1-20) (Mar. 1, 2019).

Hauser, S.L., et al., "Evaluation of Fenebrutinib, a Highly Selective BTKi, on Disease Progression of Multiple Sclerosis" Poster (P0211) 8th Joint ACTRIMS-ECTRIMS Meeting, Virtual, pp. 1-10 (Sep. 11-13, 2020).

Anonymous: "History of Changes for Study: NCT04586023" Oct. 8, 2020 (Oct. 8, 2020) Retrieved from the Internet: Nov. 29, 2022, pp. 1-7 https://clinicaltrials.gov/ct2/history/NCT04586023?A=1&B=1&C-merged#StudyPageTop.

(Continued)

*Primary Examiner* — Timothy R Rozof

(74) *Attorney, Agent, or Firm* — Armstrong Teasdale LLP

(57) ABSTRACT

Provided herein are methods of treating Relapsing Multiple Sclerosis (RMS) in a subject in need thereof, by administering to the subject about 200 mg of fenebrutinib twice daily, or an equivalent amount of a pharmaceutically acceptable salt thereof.

17 Claims, 2 Drawing Sheets

(56) References Cited

OTHER PUBLICATIONS

International Preliminary Report on Patentability—PCT/US2021/025301 issued Sep. 29, 2022, pp. 1-10.
International Search Report with Written Opinion—PCT/US2021/025301 mailed May 27, 2021, pp. 1-15.
Iyer, A.S., et al., "Absence of Tec family kinases interleukin-2 inducible T cell kinase (Itk) and Bruton's tyrosine kinase (Btk) severely impairs Fc epsilonRI-dependent mast cell responses" J Biol Chem 286(11):9503-9513 (Mar. 18, 2011).
Johnson, A.R., et al., "Fenebrutinib, a Potent, Highly Selective, Noncovalent BTK Inhibitor for the Treatment of Multiple Sclerosis" Poster (P0338) 8th Joint ACTRIMS-ECTRIMS Meeting, Virtual, pp. 1-10 ( Sep. 11-13, 2020).
Lassmann, H., et al., "Multiple Sclerosis Pathology" Cold Spring Harb Perspect Med 8(3):a2028936 (1-15) (Mar. 1, 2018).
Lassmann, H., "Pathogenic Mechanisms Associated With Different Clinical Courses of Multiple Sclerosis" Front Immunol 9:Art. No. 3116 (1-14) (Jan. 1, 2019).
Niiro, H., et al., "Regulation of B-cell fate by antigen-receptor signals" Nat Rev Immunol 2(12):945-956 (Dec. 1, 2002).
Noonan, C.W., et al., "Prevalence estimates for MS in the United States and evidence of an increasing trend for women" Neurology 58(1):136-138 (Jan. 8, 2002).
Oh, J., et al., "The Safety of Fenebrutinib in a Large Population of Patients With Diverse Autoimmune Indications Supports Investigation in Multiple Sclerosis" Slides (Presentation: S25.005) AAN Virtual Annual Meeting, pp. 1-12 ( Apr. 17-22, 2021).
Reth, M., et al. Advances in Immunology "Chapter Four—Signaling Circuits in Early B-Cell Development" Austen, F., et al., eds., First edition, San Diego, CA—USA:Academic Press, vol. 122:129-175 (2014).
US Clinical TRIALS.gov, "A Study to Evaluate the Efficacy and Safety of Fenebrutinib Compared With Teriflunomide in Relapsing Multiple Sclerosis (RMS) (FENhance)" (ClinicalTrials.gov Identifier: NCT04586010; History of Changes, Submitted Date: Oct. 8, 2020 (v1); First Posted: Oct. 14, 2020; Last Update Posted: Oct. 14, 2020 [Actual]; Retrieved: Aug. 8, 2023; Sponsor: Hoffmann-La Roche; pp. 1-13) https://www.clinicaltrials.gov/study/NCT04586010?term=fenebrutinib&rank=5&tab=history&a=1.
US Clinical TRIALS.gov, "A Study to Evaluate the Efficacy and Safety of Fenebrutinib Compared With Teriflunomide in Relapsing Multiple Sclerosis (RMS) (FENhance)" (ClinicalTrials.gov Identifier: NCT04586010; History of Changes, Submitted Date: Mar. 10, 2021 (v5); First Posted: Oct. 14, 2020; Last Update Posted: Mar. 11, 2021 [Actual]; Retrieved: Aug. 9, 2023; Sponsor: Hoffmann-La Roche) pp. 1-14 https://www.clinicaltrials.gov/study/NCT04586010?term=fenebrutinib&rank=5&tab=history&a=5.
US Clinical TRIALS.gov, "Study to Evaluate the Efficacy and Safety of Fenebrutinib Compared With Teriflunomide in Relapsing Multiple Sclerosis (RMS) (FENhance 2)" (ClinicalTrials.gov Identifier: NCT04586023; History of Changes, Submitted Date Mar. 10, 2021 (v5); First Posted: Oct. 14, 2020; Last Update Posted Mar. 11, 2021 [Actual]; Retrieved: Aug. 8, 2023; Sponsor: Hoffmann-La Roche) pp. 1-14 https://www.clinicaltrials.gov/study/NCT04586023?term=fenebrutinib&rank=4&tab=history&a=5.
US Clinical TRIALS.gov, "Study to Evaluate the Efficacy and Safety of Fenebrutinib Compared With Teriflunomide in Relapsing Multiple Sclerosis (RMS) (FENhance 2)" (ClinicalTrials.gov Identifier: NCT04586023; History of Changes, Submitted Date: Oct. 8, 2020 (v1); First Posted: Oct. 14, 2020; Last Update Posted: Oct. 14, 2020 [Actual]; Retrieved: Aug. 8, 2023; Sponsor: Hoffmann-La Roche) pp. 1-13 https://www.clinicaltrials.gov/study/NCT04586023?term=fenebrutinib&rank=4&tab=history&a=1.
Wallin, M.T., et al., "Global, regional, and national burden of multiple sclerosis 1990-2016: a systematic analysis for the Global Burden of Disease Study 2016" Lancet Neurol 18(3):269-285 (Mar. 1, 2019).
Weber, M., et al., "Fenebrutinib reduces disease activity in a mouse model of inflammatory multiple sclerosis, which is associated with reduced microglial activation" Poster (P680) 37th Congress of the European Committee for Treatment and Research in Multiple Sclerosis [ECTRIMS], Virtual, pp. 1 (Oct. 13-15, 2021).
Weber, M.S., et al., "Compared with Evobrutinib and Tolebrutinib, Fenebrutinib Displays Highest In Vitro Potency on both B Cells and Myeloid Progenitor Lineage Cells" Poster (P15.091) AAN 2021 Annual Meeting, Virtual, pp. 1-5 ( Apr. 17-22, 2021).
Wexler, M., et al., "EMD Serono Opening Phase 3 Trials of Oral Evobrutinib in Relapsing MS Patients" Multiple Sclerosis News Today: 1-3 (Sep. 23, 2019) https://multiplesclerosisnewstoday.com/news-posts/2019/09/11/emd-serono-initiates-pivotal-phase-iii-program-for-investigational-evobrutinib-in-relapsing-multiple-sclerosis/.
Wexler, M., et al., "Fewer New Brain Lesions Seen in Patients Treated with BTK Blocker in Phase 2 Trial, Results Show" Multiple Sclerosis News Today: 1-2 (Feb. 7, 2020) https://multiplesclerosisnewstoday.com/news-posts/2020/02/06/sanofi-brain-penetrant-btk-inhibitor-meets-primary-endpoint-of-phase-2-trial-in-relapsing-multiple-sclerosis/.
Bar-Or, A., "The Immunology of Multiple Sclerosis," Semin. Neurol., 2008, vol. 28, No. 1, pp. 29-45.
Burger, L., "Sanofi's mixed fortunes in MS drug trials has market focus on win," Reuters, Sep. 2, 2024, 19 pages, available from https://url.usb.m.mimecastprotect.com/s/ylXmC93vLniNrWmKuOs0CqnsPu?domain=reuters.com/.
Dendrou et al., "Immunopathology of multiple sclerosis", Nature Reviews Immunology, 2015, vol. 15, pp. 545-558.
Filippi et al., "Multiple Sclerosis," Nature Reviews, Disease Primers, 2018, vol. 4:43, pp. 1-27.
Fox et al., "Tolebrutinib in Nonrelapsing Secondary Progressive Multiple Sclerosis", N. Engl. J. Med., 2025, vol. 392, No. 19, pp. 1883-1892.
Kholodov et al., "Clinical pharmacokinetics" Manual (English translation), Moskva "Meditsina" 1985, 29 pages.
Oh, et al., "Tolebrutinib versus Teriflunomide in Relapsing Multiple Sclerosis," N. Engl. J. Med., 2025, vol. 392, No. 19, pp. 1893-1904.
Sergeev, P.V., "Concise Course in Molecular Pharmacology," English translation, Moscow: Ministry of Health of the Russian Federation, II Pirogov Russian National Research Medical University, Moscow, 1975, 2 pages.
Ziemssen et al., "Optimizing treatment success in multiple sclerosis", J. Neurol, 2016, vol. 263, pp. 1053-1065.

* cited by examiner

METHODS OF TREATING RELAPSING MULTIPLE SCLEROSIS USING AN INHIBITOR OF BRUTON'S TYROSINE KINASE

CROSS-REFERENCE TO RELATED APPLICATIONS

This application is a National Stage Entry under 35 U.S.C. § 371 of International Application No. PCT/US2021/025301, filed Apr. 1, 2021, which claims the benefit of priority of U.S. Provisional Application Ser. No. 63/051,767, filed Jul. 14, 2020; and U.S. Provisional Application Ser. No. 63/005,095, filed Apr. 3, 2020; the disclosures of each of which are incorporated herein by reference in their entireties.

FIELD

The present disclosure relates to methods of treating relapsing multiple sclerosis (RMS) using an inhibitor of Bruton's tyrosine kinase (BTK).

BACKGROUND

Bruton's Tyrosine Kinase (BTK): Discovery of the genetic basis for primary immunodeficiencies has been the source of new therapeutic targets in immunomodulatory therapies. In humans, mutations in the gene for Bruton's tyrosine kinase (BTK), which is located on the X chromosome, can result in the development of an immunodeficiency state characterized by a significant absence of circulating B cells (Bruton O C. Pediatrics 1952, 9:722-8; Conley M E, et al, Immunol Rev 2005, 203:216-34), and very low immunoglobulin levels due to a defect in B-cell differentiation at the pro- to pre-B cell stage that precludes assembly of the B-cell receptor (BCR) complex and immunoglobulin gene expression (Reth M, Nielsen P., Adv Immunol 2014, 122: 129-75. doi: 10.1016/B978-0-12-800267-4.00004-3). Affected male patients have a primary immune deficiency, X-linked agammaglobulinemia (XLA), and are susceptible to recurrent infections starting shortly after birth. Patients with XLA can live relatively normal lives on a standard therapy of intravenous (IV) immunoglobulin, which suggests that BTK can be safely inhibited, especially in people with established immune systems. IV immunoglobulin replacement therapy lowers the rate of infection, reduces hospitalization rates for patients with XLA, and has greatly improved the long-term prognosis of these patients.

BTK is essential for the differentiation and activity of B cells during immune system ontogeny and normal adaptive immune responses. BTK is activated by phosphatidylinositol 3-kinase-dependent plasma membrane recruitment and phosphorylation on tyrosine Y551 by the Src-family kinase Lyn. Autophosphorylation and activation also occurs on tyrosine Y223 in a BTK-specific manner. Once activated, BTK induces PLCγ2- and $Ca^{2+}$-dependent signaling, which leads to the activation of NF-κB- and NFAT-dependent pathways leading to cellular activation and differentiation (Niiro H, Clark E A., Nat Rev Immunol 2002, 2:945-56). In addition, BTK is important in FcεRI signaling in both basophils and mast cells. BTK null mice have impaired FcεRI signaling resulting in decreased histamine and inflammatory cytokine release (Iyer A S, et al., J Bio Chem 2011, 286:9503-13. doi: 10.1074/jbc.M110.1656131).

Multiple Sclerosis: Multiple sclerosis (MS) is a chronic, inflammatory, demyelinating, and degenerative disease of the CNS that affects approximately 900,000 people in the United States (Wallin et al. 2019) and 2.3 million worldwide (GBD 2016 Multiple Sclerosis Collaborators 2019). It is primarily a disease of young adults, with 70%-80% of patients having an age of onset (i.e., initial clinical presentation to a physician) between 20 and 40 years (Anderson et al. 1992; Noonan et al. 2002) and has a gender bias influenced by the phenotype, with approximately up to 64%-70% of diagnosed patients being women (Anderson et al. 1992; Noonan et al. 2002).

Traditionally, MS is classified into three clinical phenotypes, one of which is relapsing MS (RMS). Relapsing MS (RMS) forms encompass RRMS and active SPMS. Without wishing to be bound by any theory, disability progression across the spectrum of MS might occur as a result of two concurrent inflammatory mechanisms: active inflammation and chronic compartmentalized inflammation. These two types of inflammation may contribute in different extents across the different types and stages of MS.

RMS is associated with an active inflammatory mechanism characterized by focal, bulk T-cell, and B-cell invasion and blood brain barrier leakage that give rise to classic active demyelinating plaques in the white matter. Chronic compartmentalized inflammation is responsible for an increase in disability that occurs independently of relapses or DA and is characterized by demyelination and axonal loss (progression biology; Lassmann et al. 2019). While this aspect of inflammation is considered the hallmark of progressive forms of MS, RMS phenotypes also harbor signs of progression biology/chronic compartmentalized inflammation, which expresses itself as a chronic and slow accumulation of T cells and B cells without leakage of the blood brain barrier and may create subpial-demyelinated lesions in the cerebral and cerebellar cortex, as well as a slow expansion of pre-existing lesions in the white matter and diffuse chronic inflammation in the normal appearing white and gray matter (Lassmann 2018). Finally, the role of the myeloid lineage cells, including macrophages and microglia, may also impact both pathological and clinical outcomes (Absinta et al, 2020).

In vitro cell-based experiments suggest that antagonism of BTK with fenebrutinib leads to inhibition of BCR-dependent B-cell proliferation and a reduction of inflammatory cytokine production from myeloid cells (including tumor necrosis factor-α [TNF-α]). Myeloid effector functions are triggered by immune complexes in vitro and increasing evidence suggests that B cells and myeloid/microglia may be central to the immunopathology of MS.

As a result, the salient features of disease remain under addressed in all forms of MS, and treatments for RMS represent a serious unmet medical need.

SUMMARY OF THE DISCLOSURE

Provided herein are methods and uses of a BTK inhibitor, fenebrutinib, or a pharmaceutically acceptable salt of fenebrutinib, for treating Relapsing Multiple Sclerosis (RMS).

E1. In a first embodiment (Embodiment 1, "E1"), provided herein is a method of treating relapsing multiple sclerosis (RMS) in a subject in need thereof, comprising administering to the subject about 200 mg fenebrutinib twice daily, or an equivalent amount of a pharmaceutically acceptable salt thereof.

E2. A method of reducing Annualized Relapse Rate (ARR) and reducing the risk of experiencing cCDP12 in a subject with RMS, comprising administering to the subject about 200 mg fenebrutinib twice daily, or an equivalent amount of a pharmaceutically acceptable salt thereof.

E2a. A method of reducing Annualized Relapse Rate (ARR) in a subject with RMS, comprising administering to the subject about 200 mg fenebrutinib twice daily, or an equivalent amount of a pharmaceutically acceptable salt thereof.

E2b. A method of reducing the risk of experiencing cCDP12 in a subject with RMS, comprising administering to the subject about 200 mg fenebrutinib twice daily, or an equivalent amount of a pharmaceutically acceptable salt thereof.

E2c. The method of E2b, wherein cCDP12 comprises the first occurrence of a progression event in the subject after beginning of administration of fenebrutinib or a pharmaceutically acceptable salt thereof, wherein the progression event is confirmed at least 12 weeks after the initial disability progression.

E2d. A method of increasing time to onset of cCDP12 in a subject with RMS, comprising administering to the subject about 200 mg fenebrutinib twice daily, or an equivalent amount of a pharmaceutically acceptable salt thereof, wherein time to onset of cCDP12 comprises the period from before beginning administration of fenebrutinib or a pharmaceutically acceptable salt thereof to the first occurrence of a progression event, wherein the progression event is confirmed at least 12 weeks after the initial disability progression.

E2e. The method of E2c or E2d, wherein the progression event is one of:

(a) an increase from baseline in Expanded Disability Status Scale (EDSS) score of ≥1.0 point in a subject with a baseline EDSS score of ≤5.5 or an increase of ≥0.5 points in a subject with a baseline EDSS score of >5.5 (confirmed disability progression [CDP]);

(b) ≥20% increase from baseline in the Timed 25-Foot Walk Test (T25FWT); or (c) ≥20% increase from baseline in time to complete the 9-Hole Peg Test (9-HPT).

E3. The method of any one of E1 to E2e, further comprising evaluating disability progression in the subject.

E4. The method of E3, wherein disability progression is evaluated using the Expanded Disability Status Scale (EDSS), the 9-Hole Peg Test (9-HPT), or the Timed 25-Foot Walk Test (T25FWT), or any combinations thereof.

E5. The method of any one of E1 to E4, comprising evaluating the onset of composite 12-week confirmed disability progression (cCDP12), wherein onset of cCDP12 comprises at least one of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; or (c) increase from baseline of at least 20% in T25FWT;

and wherein the change from baseline is confirmed at least 12 weeks after the initial increase.

E6. The method of any one of E1 to E5, comprising evaluating the onset of 12-week confirmed disability progression (CDP12) in the subject, wherein the onset of CDP12 comprises an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points; and wherein the change in EDSS score is confirmed at least 12 weeks after the initial increase.

E7. The method of any one of E1 to E6, comprising evaluating the onset of composite 24-week confirmed disability progression (cCDP24), wherein the onset of cCDP24 comprises the subject experiencing at least one of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; or (c) increase from baseline of at least 20% in T25FWT;

and wherein the change from baseline is confirmed at least 24 weeks after the initial increase.

E8. The method of any one of E1 to E7, comprising evaluating the onset of 24-week confirmed disability progression (CDP24) in the subject, wherein the onset of CDP24 comprises an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points; and wherein the change in EDSS score is confirmed at least 24 weeks after the initial increase.

E9. The method of any one of E1 to E8, wherein time to progression in the subject is increased, wherein progression comprises:

an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points.

E10. The method of any one of E1 to E9, wherein time to progression in the subject is increased, wherein the progression comprises an increase from baseline of at least 20% in time to complete the 9-HPT.

E11. The method of any one of E1 to E10, wherein time to progression in the subject is increased, wherein the progression comprises an increase from baseline of at least 20% in T25FWT.

E12. The method of any one of E1 to E11, wherein time to progression in the subject in increased in comparison to a subject with RMS who is not administered fenebrutinib or a pharmaceutically acceptable salt thereof.

E13. The method of any one of E1 to E12, wherein time to progression in the subject is increased in comparison to a subject with RMS who is administered a small molecule inhibitor of dihydroorotate dehydrogenase.

E14. The method of any one of E1 to E13, wherein the time to progression in the subject is increased at least 5%, at least 10%, at least 15%, at least 20%, at least 25%, at least 30%, or at least 35%.

E15. The method of any one of E1 to E14, wherein time to onset of CDP12 in the subject is increased.

E16. The method of any one of E1 to E15, wherein time to onset of cCDP12 in the subject is increased.

E17. The method of any one of E1 to E16, wherein time to onset of CDP24 in the subject is increased.

E18. The method of any one of E1 to E17, wherein time to onset of cCDP24 in the subject is increased.

E18a. The method of any one of E1 to E18, wherein the time to onset is increased at least 5%, at least 10%, at least 15%, at least 20%, at least 25%, at least 30%, or at least 35%.

E19. The method of any one of E15 to E18a, wherein the time to onset in the subject is increased in comparison to another subject with RMS who is not administered fenebrutinib or a pharmaceutically acceptable salt thereof.

E20. The method of any one of E15 to E19, wherein time to progression in the subject is increased in comparison to another subject with RMS who is administered a small molecule inhibitor of dihydroorotate dehydrogenase.

E21. The method of any one of E15 to E20, wherein the time to progression in the subject is increased at least 5%, at least 10%, at least 15%, at least 20%, at least 25%, at least 30%, or at least 35%.

E22. The method of any one of E1, or E3 to E21, wherein the risk of the subject experiencing cCDP12 is reduced.

E23. The method of any one of E1 to E22, wherein the risk of the subject experiencing CDP12 is reduced.

E24. The method of any one of E1 to E23, wherein the risk of the subject experiencing cCDP24 is reduced.

E25. The method of any one of E1 to E24, wherein the risk of the subject experiencing CDP24 is reduced.

E26. The method of any one of E2 to E25, wherein the risk is reduced by greater than 20%, greater than 25%, greater than 30%, greater than 35%, greater than 40%, greater than 45%, or greater than 50%.

E27. The method of any one of E2 to E26, wherein the risk is reduced over a time period of about 12 weeks, about 24 weeks, about 36 weeks, about 48 weeks, about 72 weeks, or about 96 weeks after beginning administration of fenebrutinib or a pharmaceutically acceptable salt thereof.

E28. The method of any one of E2 to E27, wherein the risk is reduced relative to another subject with RMS who is not administered fenebrutinib or a pharmaceutically acceptable salt thereof.

E29. The method of any one of E2 to E28, wherein the risk is reduced relative to a subject with RMS who is administered a small molecule inhibitor of dihydroorotate dehydrogenase.

E30. The method of any one of E1 to E29, further comprising evaluating the annualized relapse rate of the subject.

E31. The method of any one of E1 or E2b to E30, wherein the annualized relapse rate of the subject is reduced.

E32. The method of any one of E1 to E31, wherein the annualized relapse rate of the subject is reduced by at least 20%, at least 25%, at least 30%, at least 35%, at least 40%, at least 45%, at least 50%, at least 55%, or at least 60%.

E33. The method of any one of E2 to E32, wherein the annualized relapse rate of the subject is reduced relative to another subject with RMS who is not administered fenebrutinib or a pharmaceutically acceptable salt thereof.

E34. The method of any one of E2 to E33, wherein the annualized relapse rate of the subject is reduced relative to another subject with RMS who is administered a small molecule inhibitor of dihydroorotate dehydrogenase.

E35. The method of any one of E1 to E34, further comprising evaluating the number of T1 Gd+ lesions in the subject.

E36. The method of any one of E1 to E35, further comprising evaluating the number of new and/or enlarging T2 hyperintense lesions in the subject.

E37. The method of E35 or E36, wherein the number of lesions is evaluated 12 weeks, 24 weeks, 48 weeks, or 96 weeks, or any combinations thereof, after beginning administration of fenebrutinib or a pharmaceutically acceptable salt thereof.

E38. The method of any one of E1 to E37, wherein the number of T1 Gd+ lesions in the subject is reduced.

E39. The method of any one of E1 to E38, wherein the number of new and/or enlarging T2 hyperintense lesions in the subject is reduced.

E40. The method of E38 or E40, wherein the number of lesions is reduced over 12 weeks, 24 weeks, 48 weeks, or 96 weeks after beginning administration of fenebrutinib or a pharmaceutically acceptable salt thereof.

E41. The method of any one of E38 to E40, wherein the number of lesions is reduced relative to another subject with RMS who is not administered fenebrutinib or a pharmaceutically acceptable salt thereof.

E42. The method of any one of E38 to E41, wherein the number of lesions is reduced relative to another subject with RMS who is administered a small molecule inhibitor of dihydroorotate dehydrogenase.

E43. The method of any one of E1 or E3 to E42, wherein the risk of cCDP12 in the subject is reduced, and the annualized relapse rate of the subject is reduced, after beginning administration of fenebrutinib or a pharmaceutically acceptable salt thereof.

E44. The method of any one of E2 to E43, wherein the risk reduction and annualized relapse rate reduction are independently greater than 25%, greater than 30%, greater than 35%, or greater than 40%.

E45. The method of any one of E2 to E44, wherein the risk reduction and annualized relapse rate reduction are relative to another subject with RMS who is not administered fenebrutinib or a pharmaceutically acceptable salt thereof, and is optionally administered a small molecule inhibitor of dihydroorotate dehydrogenase.

E45a. The method of any one of E2d to E45, wherein time to onset of cCDP12 in the subject is reduced relative to another subject with RMS who is not administered fenebrutinib or a pharmaceutically acceptable salt thereof.

E45b. The method of any one of E2d to E45a, wherein time to onset of cCDP12 in the subject is reduced relative to another subject with RMS who is administered a small molecule inhibitor of dihydroorotate dehydrogenase.

E45c. The method of any one of E2d to E45b, wherein time to onset of cCDP12 is reduced by greater than 10%, greater than 20%, greater than 25%, greater than 30%, greater than 35%, greater than 40%, greater than 45%, or greater than 50%.

E46. A method of reducing the annualized relapse rate in a subject with relapsing multiple sclerosis (RMS) in need thereof, the method comprising administering to the subject about 200 mg fenebrutinib twice per day, or an equivalent amount of a pharmaceutically acceptable salt thereof.

E47. The method of E46, wherein the risk of the subject experiencing progression is reduced, wherein progression comprises at least one of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; or (c) increase from baseline of at least 20% in T25FWT; and wherein the change from baseline is confirmed at least 12 weeks after the initial increase.

E48. A method of reducing the risk of a subject with RMS experiencing progression, the method comprising administering to the subject about 200 mg fenebrutinib twice daily, or an equivalent amount of a pharmaceutically acceptable salt thereof, wherein progression comprises at least one of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; or (c) increase from baseline of at least 20% in T25FWT; and wherein the change from baseline is confirmed at least 12 weeks after the initial increase.

E49. The method of E48, wherein the annualized relapse rate of the subject is reduced.

E50. The method of E46, E47, or E49, wherein the reduction of annualized relapse rate is greater than 25%, greater than 30%, greater than 35%, greater than 40%, or greater than 45%.

E51. The method of any one of E47 to E50, wherein the risk is reduced by greater than 25%, greater than 30%, greater than 35%, greater than 40%, or greater than 45%.

E52. The method of any one of E46 to E51, wherein the reduction is relative to another subject with RMS who is not administered fenebrutinib or a pharmaceutically acceptable salt thereof.

E53. The method of any one of E46 to E52, wherein the reduction is relative to another subject with RMS who is administered a small molecule inhibitor of dihydroorotate dehydrogenase.

E54. The method of any one of E46 to E53, wherein the reduction is over 12 weeks, 24 weeks, 48 weeks, 52 weeks, or 96 weeks after the subject begins administration of fenebrutinib or a pharmaceutically acceptable salt thereof.

E55. The method of any one of E1 to E54, wherein the method further comprises the step of measuring one or more clinical or laboratory endpoints in the subject in order to evaluate the efficacy of treating RMS.

E56. The method of E55, wherein the one or more clinical or laboratory endpoints are selected from the group consisting of the subject's MSIS-29, Neuro-QoL Upper Extremity, PROMIS-FatigueMS, MSWS-12, PGI-S, WPAI:MS, PGI-C, EQ-5D-5L, C-SSRS, 9-HPT, T25FWT, EDSS, SDMT, or MRI.

E57. The method of E55 or E56, wherein the clinical or laboratory endpoint is measured 2 weeks, 6 weeks, 12 weeks, 18 weeks, 24 weeks, 36 weeks, 48 weeks, 60 weeks, 72 weeks, 84 weeks, 96 weeks, 108 weeks, or 120 weeks, or any combinations thereof, after beginning administration of fenebrutinib, or a pharmaceutically acceptable salt thereof.

E58. The method of any one of E1 to E57, wherein the fenebrutinib or pharmaceutically acceptable salt thereof is administered orally.

E59. The method of any one of E1 to E58, wherein the fenebrutinib or pharmaceutically acceptable salt thereof is administered in the form of one or more tablets or capsules.

E60. The method of any one of E1 to E59, wherein the fenebrutinib or pharmaceutically acceptable salt thereof is administered in the form of two tablets twice daily, each tablet comprising about 100 mg fenebrutinib or an equivalent amount of a pharmaceutically acceptable salt thereof.

E61. The method of any one of E1 to E60, wherein the free form of fenebrutinib is administered.

E62. The method of any one of E1 to E61, wherein the subject has relapsing-remitting MS.

E63. The method of any one of E1 to E62, wherein the subject has active secondary progressive MS.

E64. A compound for use in the treatment of relapsing multiple sclerosis (RMS) in a subject in need thereof, wherein the compound is fenebrutinib or a pharmaceutically acceptable salt thereof, and wherein the treatment comprises administering to the subject about 200 mg fenebrutinib twice daily, or an equivalent amount of a pharmaceutically acceptable salt thereof.

E65. A compound for use in reducing Annualized Relapse Rate (ARR) and reducing the risk of experiencing cCDP12 in a subject with RMS, wherein the compound is fenebrutinib or a pharmaceutically acceptable salt thereof, and wherein reducing ARR and reducing the risk of experiencing cCDP12 comprises administering to the subject about 200 mg fenebrutinib twice daily, or an equivalent amount of a pharmaceutically acceptable salt thereof.

E65a. A compound for use in reducing Annualized Relapse Rate (ARR) in a subject with RMS, wherein the compound is fenebrutinib or a pharmaceutically acceptable salt thereof, and wherein reducing ARR comprises administering to the subject about 200 mg fenebrutinib twice daily, or an equivalent amount of a pharmaceutically acceptable salt thereof.

E65b. A compound for use in reducing the risk of experiencing cCDP12 in a subject with RMS, wherein the compound is fenebrutinib or a pharmaceutically acceptable salt thereof, and wherein reducing the risk of experiencing cCDP12 comprises administering to the subject about 200 mg fenebrutinib twice daily, or an equivalent amount of a pharmaceutically acceptable salt thereof.

E65c. The compound for use of E65b, wherein cCDP12 comprises the first occurrence of a progression event in the subject after beginning of administration of fenebrutinib or a pharmaceutically acceptable salt thereof, wherein the progression event is confirmed at least 12 weeks after the initial disability progression.

E65d. A compound for use in reducing time to onset of cCDP12 in a subject with RMS, wherein the compound is fenebrutinib or a pharmaceutically acceptable salt thereof, wherein reducing time to onset of cCDP12 comprises administering to the subject about 200 mg fenebrutinib twice daily, or an equivalent amount of a pharmaceutically acceptable salt thereof, and wherein time to onset of cCDP12 comprises the period from before beginning administration of fenebrutinib or a pharmaceutically acceptable salt thereof to the first occurrence of a progression event, wherein the progression event is confirmed at least 12 weeks after the initial disability progression.

E65e. The compound for use of E65c or E65d, wherein the progression event is one of:

(a) an increase from baseline in Expanded Disability Status Scale (EDSS) score of 1.0 point in a subject with a baseline EDSS score of ≤5.5 or an increase of ≥0.5 points in a subject with a baseline EDSS score of >5.5 (confirmed disability progression [CDP]);

(b) ≥20% increase from baseline in the Timed 25-Foot Walk Test (T25FWT); or (c) ≥20% increase from baseline in time to complete the 9-Hole Peg Test (9-HPT).

E66. The compound for use of any one of E64 to E65e, wherein the treatment comprises evaluating disability progression in the subject.

E67. The compound for use of E66, wherein disability progression is evaluated using the Expanded Disability Status Scale (EDSS), the 9-Hole Peg Test (9-HPT), or the Timed 25-Foot Walk Test (T25FWT), or any combinations thereof.

E68. The compound for use of any one of E63 to E67, wherein the treatment comprises evaluating the onset of composite 12-week confirmed disability progression (cCDP12), wherein onset of cCDP12 comprises at least one of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; or (c) increase from baseline of at least 20% in T25FWT;

and wherein the change from baseline is confirmed at least 12 weeks after the initial increase.

E69. The compound for use of any one of E64 to E68, wherein the treatment comprises evaluating the onset of 12-week confirmed disability progression (CDP12) in the subject, wherein the onset of CDP12 comprises an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points; and wherein the change in EDSS score is confirmed at least 12 weeks after the initial increase.

E70. The compound for use of any one of E64 to E69, wherein the treatment comprises evaluating the onset of composite 24-week confirmed disability progression (cCDP24), wherein the onset of cCDP24 comprises the subject experiencing at least one of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; or (c) increase from baseline of at least 20% in T25FWT;

and wherein the change from baseline is confirmed at least 24 weeks after the initial increase.

E71. The compound for use of any one of E64 to E70, wherein the treatment comprises evaluating the onset of 24-week confirmed disability progression (CDP24) in the subject, wherein the onset of CDP24 comprises an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points; and wherein the change in EDSS score is confirmed at least 24 weeks after the initial increase.

E72. The compound for use of any one of E64 to E71, wherein time to progression in the subject is increased, wherein progression comprises:

an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points.

E73. The compound for use of any one of E64 to E72, wherein time to progression in the subject is increased, wherein the progression comprises increase from baseline of at least 20% in time to complete the 9-HPT.

E74. The compound for use of any one of E64 to E73, wherein time to progression in the subject is increased, wherein the progression comprises an increase from baseline of at least 20% in T25FWT.

E75. The compound for use of any one of E64 to E74, wherein time to progression in the subject in increased in comparison to a subject with RMS who is not administered fenebrutinib or a pharmaceutically acceptable salt thereof.

E76. The compound for use of any one of E64 to E75, wherein time to progression in the subject is increased in comparison to a subject with RMS who is administered a small molecule inhibitor of dihydroorotate dehydrogenase.

E77. The compound for use of any one of E64 to E76, wherein the time to progression in the subject is increased at least 5%, at least 10%, at least 15%, at least 20%, at least 25%, at least 30%, or at least 35%.

E78. The compound for use of any one of E64 to E77, wherein time to onset of CDP12 in the subject is increased.

E79. The compound for use of any one of E64 to E78, wherein time to onset of cCDP12 in the subject is increased.

E80. The compound for use of any one of E64 to E79, wherein time to onset of CDP24 in the subject is increased.

E81. The compound for use of any one of E64 to E80, wherein time to onset of cCDP24 in the subject is increased.

E81a. The compound for use of any one of E64 to E81, wherein the time to onset is increased at least 5%, at least 10%, at least 15%, at least 20%, at least 25%, at least 30%, or at least 35%.

E82. The compound for use of any one of E78 to E81a, wherein the time to onset in the subject is increased in comparison to another subject with RMS who is not administered fenebrutinib or a pharmaceutically acceptable salt thereof.

E83. The compound for use of any one of E78 to E82, wherein time to progression in the subject is increased in comparison to another subject with RMS who is administered a small molecule inhibitor of dihydroorotate dehydrogenase.

E84. The compound for use of any one of E78 to E83, wherein the time to progression in the subject is increased at least 5%, at least 10%, at least 15%, at least 20%, at least 25%, at least 30%, or at least 35%.

E85. The compound for use of any one of E64 or E66 to E84, wherein the risk of the subject experiencing cCDP12 is reduced.

E86. The compound for use of any one of E64 to E85, wherein the risk of the subject experiencing CDP12 is reduced.

E87. The compound for use of any one of E64 to E86, wherein the risk of the subject experiencing cCDP24 is reduced.

E88. The compound for use of any one of E64 to E87, wherein the risk of the subject experiencing CDP24 is reduced.

E89. The compound for use of any one of E65 to E88, wherein the risk is reduced by greater than 20%, greater than 25%, greater than 30%, greater than 35%, greater than 40%, greater than 45%, or greater than 50%.

E90. The compound for use of any one of E65 to E89, wherein the risk is reduced over a time period of about 12 weeks, about 24 weeks, about 36 weeks, about 48 weeks, about 72 weeks, or about 96 weeks after beginning administration of fenebrutinib or a pharmaceutically acceptable salt thereof.

E91. The compound for use of any one of E65 to E90, wherein the risk is reduced relative to another subject with RMS who is not administered fenebrutinib or a pharmaceutically acceptable salt thereof.

E92. The compound for use of any one of E65 to E91, wherein the risk is reduced relative to a subject with RMS who is administered a small molecule inhibitor of dihydroorotate dehydrogenase.

E93. The compound for use of any one of E64 to E92, wherein the treatment comprises evaluating the annualized relapse rate of the subject.

E94. The compound for use of any one of E64 or E66 to E93, wherein the annualized relapse rate of the subject is reduced.

E95. The compound for use of any one of E64 to E94, wherein the annualized relapse rate of the subject is reduced by at least 20%, at least 25%, at least 30%, at leaset 35%, at least 40%, at least 45%, at least 50%, at least 55%, or at least 60%.

E96. The compound for use of any one of E65 to E95, wherein the annualized relapse rate of the subject is reduced relative to another subject with RMS who is not administered fenebrutinib or a pharmaceutically acceptable salt thereof.

E97. The compound for use of any one of E65 to E96, wherein the annualized relaspe rate of the subject is reduced relative to another subject with RMS who is aministered a small molecule inhibitor of dihydroorotate dehydrogenase.

E98. The compound for use of any one of E64 to E97, wherein the treatment further comprises evaluating the number of T1 Gd+ lesions in the subject.

E99. The compound for use of any one of E64 to E98, wherein the treatment further comprises evaluating the number of new and/or enlarging T2 hyperintense lesions in the subject.

E100. The compound for use of E98 or E99, wherein the number of lesions is evaluated 12 weeks, 24 weeks, 48 weeks, or 96 weeks, or any combinations thereof, after beginning administration of fenebrutinib or a pharmaceutically acceptable salt thereof.

E101. The compound for use of any one of E64 to E100, wherein the number of T1 Gd+ lesions in the subject is reduced.

E102. The compound for use of any one of E64 to E101, wherein the number of new and/or enlarging T2 hyperintense lesions in the subject is reduced.

E103. The compound for use of E101 or E102, wherein the number of lesions is reduced over 12 weeks, 24 weeks, 48 weeks, or 96 weeks after beginning administration of fenebrutinib or a pharmaceutically acceptable salt thereof.

E104. The compound for use of any one of E101 to E103, wherein the number of lesions is reduced relative to another subject with RMS who is not administered fenebrutinib or a pharmaceutically acceptable salt thereof.

E105. The compound for use of any one of E101 to E104, wherein the number of lesions is reduced relative to another subject with RMS who is administered a small molecule inhibitor of dihydroorotate dehydrogenase.

E106. The compound for use of any one of E64 or E66 to E105, wherein the risk of cCDP12 in the subject is reduced, and the annualized relapse rate of the subject is reduced, after beginning administration of fenebrutinib or a pharmaceutically acceptable salt thereof.

E107. The compound for use of any one of E65 to E106, wherein the risk reduction and annualized relapse rate reduction are independently greater than 25%, greater than 30%, greater than 35%, or greater than 40%.

E108. The compound for use of any one of E65 to E107, wherein the risk reduction and annualized relapse rate reduction are relative to another subject with RMS who is not administered fenebrutinib or a pharmaceutically acceptable salt thereof, and is optionally administered a small molecule inhibitor of dihydroorotate dehydrogenase.

E109. A compound for use in reducing the annualized relapse rate in a subject with relapsing multiple sclerosis (RMS) in need thereof, wherein the compound is fenebrutinib or a pharmaceutically acceptable salt thereof, and wherein reducing the annualized relapse rate comprises administering to the subject about 200 mg fenebrutinib twice per day, or an equivalent amount of a pharmaceutically acceptable salt thereof.

E110. The compound for use of E109, wherein the risk of the subject experiencing progression is reduced, wherein progression comprises at least one of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; or (c) increase from baseline of at least 20% in T25FWT;

and wherein the change from baseline is confirmed at least 12 weeks after the initial increase.

E111. A compound for use in reducing the risk of a subject with RMS experiencing progression, wherein the compound is fenebrutinib or a pharmaceutically acceptable salt thereof, and wherein reducing the risk comprises administering to the subject about 200 mg fenebrutinib twice daily, or an equivalent amount of a pharmaceutically acceptable salt thereof, wherein progression comprises at least one of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; or (c) increase from baseline of at least 20% in T25FWT;

and wherein the change from baseline is confirmed at least 12 weeks after the initial increase.

E112. The compound for use of E111, wherein the annualized relapse rate of the subject is reduced.

E113. The compound for use of E109, E110, or E112, wherein the reduction of annualized relapse rate is greater than 25%, greater than 30%, greater than 35%, greater than 40%, or greater than 45%.

E114. The compound for use of any one of E110 to E113, wherein the risk is reduced by greater than 25%, greater than 30%, greater than 35%, greater than 40%, or greater than 45%.

E115. The compound for use of any one of E109 to E114, wherein the reduction is relative to another subject with RMS who is not administered fenebrutinib or a pharmaceutically acceptable salt thereof.

E116. The compound for use of any one of E109 to E115, wherein the reduction is relative to another subject with RMS who is administered a small molecule inhibitor of dihydroorotate dehydrogenase.

E117. The compound for use of any one of E109 to E116, wherein the reduction is over 12 weeks, 24 weeks, 48 weeks, 52 weeks, or 96 weeks after the subject begins administration of fenebrutinib or a pharmaceutically acceptable salt thereof.

E118. The compound for use of any one of E64 to E117, further comprising the step of measuring one or more clinical or laboratory endpoints in the subject in order to evaluate the efficacy of treating RMS.

E119. The compound for use of E118, wherein the one or more clinical or laboratory endpoints are selected from the group consisting of the subject's MSIS-29, Neuro-QoL Upper Extremity, PROMIS-FatigueMS, MSWS-12, PGI-S, WPAI:MS, PGI-C, EQ-5D-5L, C-SSRS, 9-HPT, T25FWT, EDSS, SDMT, or MRI.

E120. The compound for use of E118 or E119, wherein the clinical or laboratory endpoint is measured 2 weeks, 6 weeks, 12 weeks, 18 weeks, 24 weeks, 36 weeks, 48 weeks, 60 weeks, 72 weeks, 84 weeks, 96 weeks, 108 weeks, or 120 weeks, or any combinations thereof, after beginning administration of fenebrutinib, or a pharmaceutically acceptable salt thereof.

E121. The compound for use of any one of E64 to E120, wherein the fenebrutinib or pharmaceutically acceptable salt thereof is administered orally.

E122. The compound for use of any one of E64 to E121, wherein the fenebrutinib or pharmaceutically acceptable salt thereof is administered in the form of one or more tablets or capsules.

E123. The compound for use of any one of E64 to E122, wherein the fenebrutinib or pharmaceutically acceptable salt thereof is administered in the form of two tablets twice daily, each tablet comprising about 100 mg fenebrutinib or an equivalent amount of a pharmaceutically acceptable salt thereof.

E124. The compound for use of any one of E64 to E123, wherein the compound is the free form of fenebrutinib.

E125. The compound for use of any one of E64 to E124, wherein the subject has relapsing-remitting MS.

E126. The compound for use of any one of E64 to E125, wherein the subject has active secondary progressive MS.

E127. Further provided herein is a compound for use in the manufacture of a medicament for use in any of the methods of E1 to E63, wherein the compound is fenebrutinib or a pharmaceutically acceptable salt thereof.

E128. The method of any one of E2 to E63, or the compound for use of any one of E64 to E126, wherein relapse comprises the subject experiencing a new or worsening neurological MS symptom, wherein the symptom persists for at least 24 hours, and wherein prior to experiencing the symptom the subject had a relatively stable or improving neurological state for at least 30 days.

E129. The method or compound for use of E128, wherein relapse comprises an increase of at least one of the following:

- increase of half a step (0.5 point) on the EDSS;
- increase of two points on one functional systems score (FSS) selected from the group consisting of pyramidal, ambulation, cerebellar, brainstem, sensory, and visual; or
- increase of one point on two or more of FSS selected from the group consisting of pyramidal, ambulation, cerebellar, brainstem, sensory, and visual.

E130. The method of any one of E2 to E63, or compound for use of any one of E64 to E126, wherein relapse comprises the subject experiencing an increase of at least one of:

- increase of half a step (0.5 point) on the EDSS;
- increase of two points on one functional systems score (FSS) selected from the group consisting of pyramidal, ambulation, cerebellar, brainstem, sensory, and visual; or
- increase of one point on two or more of FSS selected from the group consisting of pyramidal, ambulation, cerebellar, brainstem, sensory, and visual.

E131. The method or compound for use of E130, wherein prior to experiencing the increase, the subject was neurologically stable or improving for at least 30 days.

E132. The method of any one of E1 to E63, or E128 to E131, or the compound for use of any one of E64 to E126, or E128 to E131, wherein prior to beginning administration of fenebrutinib or a pharmaceutically acceptable salt thereof, the subject with RMS experienced at least two clinical relapses within the previous 2 years, or one clinical relapse within the previous 12 months; and has at least one T1Gd+ lesion on an MRI taken in the previous 12 months.

E133. The method of any one of E1 to E63, or E128 to E132, or the compound for use of any one of E64 to E126, or E128 to E132, wherein prior to beginning administration of fenebrutinib or a pharmaceutically acceptable salt thereof, the subject with RMS has an EDSS score of 0-5.5.

E134. The method of any one of E1 to E63, or E128 to E133, or the compound for use of any one of E64 to E126, or E128 to E133, wherein prior to beginning administration of fenebrutinib or a pharmaceutically acceptable salt thereof, the subject does not have an RMS disease duration of >10 years from the onset of symptoms combined with an EDSS score of <2.0

E135. The method of any one of E1 to E63, or E128 to E134, or the compound for use of any one of E64 to E126, or E128 to E134, wherein prior to beginning administration of fenebrutinib or a pharmaceutically acceptable salt thereof, the subject does not have one or more of:

alanine transaminase (ALT) or (aspartate transaminase) AST>2×upper limit of normal (ULN); total bilirubin greater than 1.5×ULN without a diagnosis of Gilbert syndrome; or persisting elevations of serum amylase or lipase greater than 2×ULN.

E136. The method of any one of E1 to E63, or E128 to E135, or the compound for use of any one of E64 to E126, or E128 to E135, wherein prior to beginning administration of fenebrutinib or a pharmaceutically acceptable salt thereof, the subject does not have:

(a) significantly impaired bone marrow function or significant anemia, leukopenia, neutropenia, or thrombocytopenia; or (b) any one of hemoglobin<9.5 g/dL, absolute white cell count<4000 cells/$mm^3$ (μL), platelet count<100 cells×$10^9$/L, or absolute neutrophil≤1500 cells/$mm^3$ (μL), or a combination of (a) and (b).

E137. Further provided herein is a method of any one of E1 to E63, or E128 to E136, or compound for use of any one of E64 to E126, or E128 to E136, wherein the subject is not concomitantly administered a strong CYP3A4 inhibitor while being administered about 200 mg fenebrutinib twice per day, or an equivalent amount of a pharmaceutically acceptable salt thereof.

E138. The method or compound for use of E137, wherein the strong CYP3A4 inhibitor is boceprevir, cobicistat, clarithromycin, danoprevir/ritonavir, elvitegravir/ritonavir, indinavir/ritonavir, itraconazole, idelalisib, ketoconazole, lopinavir/ritonavir, nefazodone, nelfinavir, posaconazole, ritonavir, saquinavir, telaprevir, telithromycin, or voriconazole.

E139. Further provided herein is a method of any one E1 to E63, or E128 to E138, or compound for use of any one of E64 to E126, or E128 to E138, wherein the subject is not concomitantly administered a strong CYP3A4 inducer while being administered about 200 mg fenebrutinib twice per day, or an equivalent amount of a pharmaceutically acceptable salt thereof.

E140. The method or compound for use of E139, wherein the strong CYP3A4 inducer is Apalutamide, carbamazepine, enzalutamide, mitotane, phenytoin, rifampin, or hyperforin (St. John's Wort).

E141. Further provided herein is a method of any one of E1 to E63, or E128 to E140, or compound for use of any one of E64 to E126, or E128 to E140, wherein the subject is not concomitantly administered a moderate CYP3A4 inducer while being administered about 200 mg fenebrutinib twice per day, or an equivalent amount of a pharmaceutically acceptable salt thereof.

E142. The method or compound for use of E141, wherein the moderate CYP3A4 inducer is Bosentan, dexamethasone, efavirenz, etravirine, phenobarbital, primidone, phenobarbital, or rifabutin.

E143. Further provided herein is a method of any one of E1 to E63, or E128 to E142, or compound for use of any one of E64 to E126, or E128 to E142, wherein the subject is not concomitantly administered a CYP3A4 substrate with a narrow therapeutic window while being administered about 200 mg fenebrutinib twice per day, or an equivalent amount of a pharmaceutically acceptable salt thereof.

E144. The method or compound for use of E143, wherein the CYP3A4 substrate with a narrow therapeutic window is alfentanil, astemizole, cyclosporine, cisapride, dihydroergotamine, ergotamine, everolimus, fentanyl, pimozide, quinidine, sirolimus, terfenadine, or tacrolimus.

DETAILED DESCRIPTION

Figure 1:
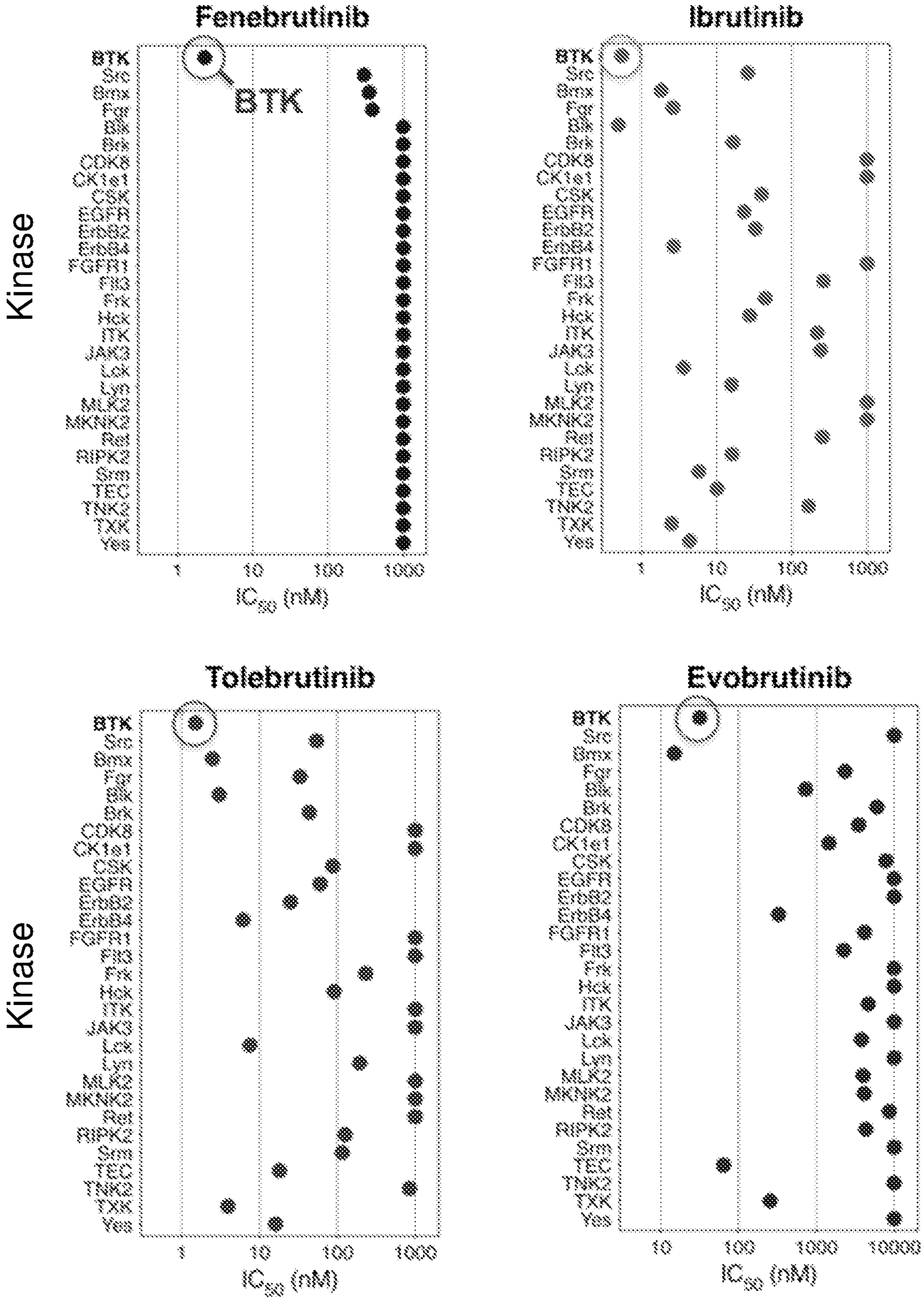
FIG. 1 depicts the comparative kinase selectivity of fenebrutinib compared to three other BTK inhibitors.

Provided herein are methods and uses of fenebrutinib, or a pharmaceutically acceptable salt of fenebrutinib, for treating Relasping Multiple Sclerosis (RMS).

Fenebrutinib is a compound of the formula:

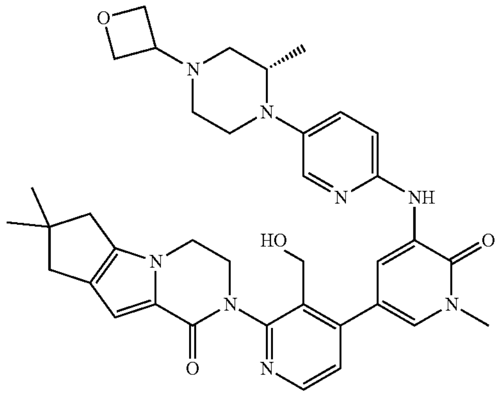 [SMILES: C[C@H]1CN(C2COC2)CCN1c1ccc(Nc2cc(-c3ccnc(N4CCn5c(cc6c5CC(C)(C)C6)C4=O)c3CO)cn(C)c2=O)nc1]

and is also known by the following names:

GDC-0853;

($6^2$S)-$2^3$-(hydroxymethyl)-$1^7$,$1^7$,$3^1$,$6^2$-tetramethyl-$1^3$,$1^4$,$1^7$,$1^8$-tetrahydro-4-aza-1(2)-cyclopenta[4,5]pyrrolo[1,2-a]pyrazina-6(1,4)-piperazina-2(2,4),3(3,5),5(2,5)-tripyridina-7(3)-oxetanaheptaphane-$1^1$($1^6$H),$3^6$($3^1$H)-dione; and (S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one.

Additional names for the same compound may be known, for example using different chemical naming schemes. The R enantiomer of the compound is: (R)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one.

Fenebrutinib is a highly selective, orally administered, reversible inhibitor of BTK. U.S. Pat. No. 8,716,274, which is hereby incorporated by reference in its entirety, discloses classes of heteroaryl pyridine and aza-pyridone compounds useful for inhibiting Btk, including fenebrutinib. WO 2017/148837, which is hereby incorporated by reference in its entirety, discloses solid forms and formulations of fenebrutinib and pharmaceutically acceptable salts thereof.

I. Definitions

It is to be understood that the terminology used herein is for the purpose of describing particular embodiments only, and is not intended to be limiting.

As used in this specification, including the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se. In some embodiments, the term "about" refers to a range of plus or minus 10% for the respective value. In some embodiments, the term "about" refers to a range of plus or minus 5% for the respective value. In some embodiments, the term "about" refers to a range of plus or minus 2% for the respective value. In some embodiments, the term "about" refers to a range of plus or minus 1% for the respective value.

It is understood that aspects and embodiments of the disclosure described herein include "comprising," "consisting," and "consisting essentially of" aspects and embodiments.

The term "pharmaceutical formulation" refers to a preparation which is in such form as to permit the biological activity of the active ingredient to be effective, and which contains no additional components which are unacceptably toxic to a subject to which the formulation would be administered. In some embodiments, such formulations are sterile. "Pharmaceutically acceptable" excipients (vehicles, additives) are those which can reasonably be administered to a subject mammal to provide an effective dose of the active ingredient employed.

As used herein, the term "treatment" refers to clinical intervention designed to alter the natural course of the individual or cell being treated during the course of clinical pathology. Desirable effects of treatment may include decreasing the rate of disease progression, ameliorating or palliating the disease state, and remission or improved prognosis. In some embodiments, two or more of such effects are achieved. In some embodiments, an individual is successfully "treated" if one or more symptoms associated with their disease or disorder is diminished; the disease or disorder is made more tolerable to the subject; the rate of degeneration or decline, or rate of disease or disorder development is slowed or stopped; the progression of the disease or disorder is slowed or stopped; or the final point of degeneration is less debilitating. For example, an individual is successfully "treated" if one or more symptoms associated with the disease (e.g., MS) are mitigated or eliminated, including, but not limited to, decreasing symptoms resulting from the disease, increasing the quality of life of those suffering from the disease, decreasing the dose of other medications required to treat the disease, and/or prolonging survival of individuals. Treatment of certain diseases or disorders may in some embodiments include, but is not limited to, specific clinical or other endpoints such as those described in the Examples provided herein.

Some embodiments described herein refer to providing a dose of fenebrutinib, or an equivalent amount of a pharmaceutically acceptable salt thereof. It would be clear to one of skill in the art how to calculate a corresponding amount of a pharmaceutical salt form of fenebrutinib, taking into account the difference in molecular weight between the free form of fenebrutinib and a salt form. For example, in some embodiments provided herein, a subject is administered about 400 mg daily of fenebrutinib (as two, 200 mg doses), or a pharmaceutically acceptable salt thereof. If a pharmaceutically acceptable salt form is administered in such embodiments, due to the salt form having a higher molecular weight than the free form of fenebrutinib, the total weight of the pharmaceutically acceptable salt of fenebrutinib administered daily is greater than 400 mg, but corresponds to about 400 mg of the free form of fenebrutinib.

A "subject" for purposes of treatment refers to any animal classified as a mammal, including humans, domestic and farm animals, and zoo, sports, or pet animals, such as dogs, horses, cats, cows, etc. In some embodiments of the methods provided herein, the subject is human. In some embodiments, the subject is a patient.

"Prior to beginning administration" may include, for example, on the same day as, but before the actual administration of, the first dose of fenebrutinib or pharmaceutically acceptable salt thereof is administered; or within one week prior to the first dose; or within two weeks prior to the first dose; or within three weeks prior to the first dose; or within four weeks prior to the first dose; or within five weeks prior to the first dose; or within six weeks prior to the first dose; or within greater than six weeks prior to the first dose; or between 1 and 28 days prior to the first dose; or within 0 to 28 days prior to the first dose. In certain embodiments, this period of time may also be referred to as "baseline". Thus, in some embodiments, baseline may include within one week prior to administering the first dose of fenebrutinib or a pharmaceutically acceptable salt thereof, including the same day just prior to administration. In other embodiments, baseline includes within one month, or within 0 to 28 days, or within six week prior to the first dose of fenebrutinib or a pharmaceutically acceptable salt thereof. In some embodiments, baseline includes the day before beginning administration, or within the week before beginning administration.

The term "biomarker" as used herein refers to an indicator, e.g., predictive, diagnostic, and/or prognostic, which can be detected in a sample. The biomarker may serve as an indicator of a particular subtype of a disease or disorder (e.g., multiple sclerosis) characterized by certain, molecular, pathological, histological, and/or clinical features. In some embodiments, a biomarker is a gene. Biomarkers may include, but are not limited to, polynucleotides (e.g., DNA, and/or RNA), polypeptides, polypeptide and polynucleotide modifications (e.g. posttranslational modifications), carbohydrates, and/or glycolipid-based molecular markers. The "amount" or "level" of a biomarker associated with an increased clinical benefit to an individual is a detectable level in a biological sample. These can be measured by methods known to one skilled in the art and also disclosed herein. The expression level or amount of biomarker assessed can, in some embodiments, be used to determine the response to the treatment. In certain embodiments, the expression level or amount of one or more biomarkers is associated with a certain response to treatment.

The term "sample," as used herein, refers to a composition that is obtained or derived from a subject and/or individual of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebrospinal fluid, saliva, sputum, tears, perspiration, mucus, tumor lysates, and tissue culture medium, tissue extracts such as homogenized tissue, tumor tissue, cellular extracts, and combinations thereof. In some embodiments, the sample is a blood sample. In other embodiments, the sample is cerebrospinal fluid (CSF).

By "tissue sample" or "cell sample" is meant a collection of similar cells obtained from a tissue of a subject or individual. The source of the tissue or cell sample may be solid tissue as from a fresh, frozen and/or preserved organ, biopsy, and/or aspirate; blood or any blood constituents such as plasma; bodily fluids such as cerebrospinal fluid, amniotic fluid, peritoneal fluid, or interstitial fluid; cells from any time in gestation or development of the subject. The tissue or cell sample may also be primary or cultured cells or cell lines. Optionally, the tissue or cell sample is obtained from a disease tissue/organ. The tissue or cell sample may contain compounds which are not naturally intermixed with the tissue in nature such as preservatives, anticoagulants, buffers, fixatives, nutrients, antibiotics, or the like.

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue. In another embodiment, a reference sample is obtained from an untreated tissue and/or cell of the body of the same subject or individual, such as, for example, a sample taken from the subject or individual prior to beginning a particular treatment (e.g., prior to beginning treatment with fenebrutinib or a pharmaceutically acceptable salt thereof). In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

The "Expanded Disability Status Scale" (EDSS) is a ClinRO measure for quantifying changes in the disability level of a subject with MS over time. The EDSS is based on a standard neurological examination, incorporating functional systems (visual, brainstem, pyramidal, cerebellar, sensory, bowel and bladder, and cerebral [or mental]) that are rated and then scored as a functional system score (FSS), and ambulation, which is scored as ambulation score. Each FSS is an ordinal clinical rating scale ranging from 0 to 5 or 6, and an ambulation score that is rated from 0 to 12. These ratings may then be used in conjunction with observations, as well as information, concerning ambulation and use of assistive devices to determine the total EDSS score. The EDSS is a disability scale that ranges in 0.5-point steps from 0 (normal) to 10.0 (death) (Kurtzke 1983; Kappos 2011). In some embodiments of the methods provided herein, the item sexual dysfunction and fatigue are not included in the EDSS score.

The "9-Hole Peg Test" (9-HPT) is a quantitative measure of upper extremity (arm and hand) function (Goodkin et al. 1988; Fischer et al. 2001). The test device consists of a container with nine pegs and a block containing nine empty holes. The subject is to pick up each of the nine pegs one at a time and as quickly as possible place them in the nine holes. Once all the pegs are in the holes, the subject is to remove them again one at a time as quickly as possible and replace them into the container. The total time to complete the task is recorded. Both the dominant and non-dominant hands are tested twice (two successfully completed trials of the dominant hand, followed immediately by two successfully completed trials of the non-dominant hand). The two trials for each hand are averaged, converted to the reciprocals of the mean times for each hand, and the two reciprocals are averaged. The 9-HPT may be administered, for example, as described in the Multiple Sclerosis Functional Composite (MSFC) Administration and Scoring Manual (Fischer et al., 2001). A meaningful change in upper extremity function may, for example, be indicated by a 20% worsening from baseline of the averaged 9-HPT times. In some embodiments, a meaningful change is >20% increase from baseline in time to complete the 9-HPT, which may also be described as an increase from baseline of at least 20% in time to complete the 9-HPT.

The "Timed 25-Foot Walk Test" (T25FWT) is a quantitative measure of mobility and leg function, based on a timed 25-foot walk. The subject is directed to start at one end of a clearly marked 25-foot course and is instructed to walk 25 feet as quickly and safely as possible, and how long it takes the subject to go from start of the walk to the end of the 25 feet is timed. In some embodiments, the task is administered immediately again by having the subject walk back the same distance, and the time for both completed trials averaged to produce the score for the T25FWT. Subjects may use assistive devices (e.g., cane or wheelchair) when performing the task. The T25FWT may be administered, for example, as described in the MSFC Administration and Scoring Manual (Fischer et al., 2001). A clinically meaningful change in mobility and leg function may, for example, be indicated by a 20% worsening from baseline of the averaged T25FWT time. In some embodiments, a meaningful change is ≥20% increase from baseline in the T25FWT, which may be described as an increase from baseline of at least 20% in T25FWT.

The "Symbol Digit Modalities Test" (SDMT) is a test used to evaluate the presence of cognitive impairment and/or changes in cognitive functioning over time and in response to treatment. The SDMT may be particularly sensitive to slowed processing of information that is commonly seen in MS (Benedict et al. 2017). The SDMT comprises a substitution task. Using a reference key, the subject has 90 seconds to pair specific numbers with given geometric figures. Responses may be collected orally, and the number of correct responses is considered the SDMT score. A clinically meaningful change in cognitive processing may, for example, be indicated by a decrease by 4 points on the SDMT score from baseline.

The "Columbia-Suicide Severity Rating Scale" (C-SSRS) is a tool used to assess the lifetime suicidality of a subject, and may be used to track suicidal events through treatment or a portion thereof. The structured interview prompts recollection of suicidal ideation, including the intensity of the ideation, behavior, and attempts with actual/potential lethality. A "baseline" C-SSRS may include, for example, C-SSRS collected prior to beginning administration of fenebrutinib or a pharmaceutically acceptable salt thereof. Such score may be compared, for example, to subsequent C-SSRS collected after beginning administration of fenebrutinib or a pharmaceutically acceptable salt thereof. Comparisons between different evaluation periods (which may, for example, occur during visits with a clinician) may be described, in some embodiments, as "since last visit" C-SSRS.

The "EQ-5D-5L" is a validated self-reported health status questionnaire that can used to calculate a health status utility score for use in health economic analyses (EuroQol Group 1990; Brooks 1996; Herdman et al. 2011; Janssen et al. 2013). There are two components to the EQ-5D-5L: a five-item health state profile that assesses mobility, self-care, usual activities, pain/discomfort, and anxiety/depression, as well as a visual analog scale (VAS) that measures health state. The EQ-5D-5L is designed to capture a subject's current health status. Published weighting systems may allow for creation of a single composite score of the subject's health status.

The "Multiple Sclerosis Impact Scale-29 Version 2" (MSIS-29, Version 2) is a 29-item subject-reported measure of the physical and psychological impacts of MS (Hobart et al. 2001). Subjects are asked to rate how much their functioning and well-being has been impacted over the past 14 days on a 4-point scale, from "Not at all" (1) to "Extremely" (4). The physical score is the sum of items 1-20, which is then transformed to a 0-100 scale. The psychological score is the sum of items 21-29, transformed to a 0-100 scale. Higher scores may indicate a greater impact of MS. A clinically meaningful impact is indicated by a change of at least 7.5 points on the physical scale in Version 1 of the MSIS-29. In Version 2 of the MSIS-29, this level of change may also indicate a meaningful impact.

The "Multiple Sclerosis Walking Scale, 12-Item" (MSWS-12) is a 12-item self-report measure of the impact of MS on the individual's ability to walk during the past 2 weeks. Each item is scored on a 5-point Likert scale, and total scores are converted to a 0-100 scale with higher scores indicating greater impact of MS on walking ability.

The "Quality of Life in Neurological Disorders, Upper Extremity" (fine motor skills and activities of daily living; Neuro-QoL, Upper Extremity) is a 20-item questionnaire used to assess upper limb function, which involves subjects with MS through each stage of its development (Gershon et al. 2012). Items include assessments of dressing, cooking, eating, cleaning, and writing from which the subject uses a 5-point Likert scale to rate his or her performance ranging from "without any difficulty" (5) to "unable to do" (1). Item scores are summed, multiplied by 100, and divided by 80; a higher score (range: 0-100) indicates better health-reported function.

The "PROMIS-FatigueMS" is an 8-item scale developed as a measure of fatigue for subjects with MS (Cook et al. 2012) with a recall period of the previous 7 days. It comprises a 5-point Likert-type scale that produces a score between 1 and 5 for each scored question. The total raw score is the sum of the values of each scored question. The total raw score ranges from 8-40. Scores can also be transformed to a PROMIS T-score where the mean is 50 and a standard deviation of 10. T-scores range from 34.7-81.3. A higher score is associated with worse fatigue.

The "Patient Global Impression of Change" (PGI-C) is a single-item assessment of a subject's impression of his or her change in MS symptoms compared with a point 6 months previous. Subjects respond on a 7-point Likert scale from "very much better" (1) to "very much worse" (7). The PGI-C is used as an anchor for determining what is a clinically meaningful change in the MSIS-29.

The "Patient Global Impression of Severity" (PGI-S) is a single-item assessment of a subject's impression of the severity of his or her MS symptoms from the past 7 days. A subject responds on a 5-point Likert scale from "none" (1) to "very severe" (5). The PGI-S is used as an anchor for determining what is a clinically meaningful change in the MSIS-29.

The "Work Productivity and Activity Impairment: Multiple Sclerosis" (WPAI:MS) is a 6-item scale. A subject estimates the amount of time that their work and daily activities were affected by their MS over the previous 7 days (Reilly et al. 1993). The WPAI:MS assesses absenteeism as well as "presenteeism," which accounts for the time when a subject was present for work or activities, but believed their health had a negative effect on their ability to perform at the usual level. A higher score represents a greater impairment in productivity.

"Confirmed Disability Progression" (CDP) refers to an increase in the subject's EDSS score that is sustained over a particular time period. This may be evaluated, for example, by calculating the subject's EDSS score, determining that the score is increased over a previous score (such as a baseline score, which may be a score taken before the subject began administration of fenebrutinib or a pharmaceutically acceptable salt thereof), and then confirming the score is still increased after a specified period of time has elapsed from the initial increase (e.g., by reevaluating the subject and recalculating it again). For example, a 12-week confirmed disability progression (CDP12) refers to an EDSS score that remains increased at least 12 weeks after the initial increase (e.g., as confirmed by recalculating the EDSS score at least 12 weeks after the initial increase). A 24-week confirmed disability progression (CDP24) refers to an EDSS score remains increased at least 24 weeks after the initial increase (e.g., as confirmed by recalculating the EDSS score at least 24 weeks after the initial increase). The initial increase may be compared to a baseline EDSS score (such as prior to beginning administration with fenebrutinib or a pharmaceutically acceptable salt thereof), or may be compared to a prior EDSS score that had remained stable over time, such as over 12, 24, 36, 48, or 60 weeks. In some embodiments, a CDP refers to an increase of ≥1.0 point from the baseline EDSS score in a subject with a baseline EDSS score of ≤5.5 points, or an increase of ≥0.5 point from the baseline EDSS score in a subject with a baseline EDSS score of >5.5 points. In certain embodiments, these CDP parameters may be described as an increase of at least 1.0 point from the baseline EDSS score in a subject with a baseline EDSS score of less than or equal to 5.5 points, or an increase of at least one 0.5 point from the baseline EDSS score in a subject with a baseline EDSS score of greater than 5.5 points. Time to onset of a CDP (e.g., time to onset of CDP12 or CDP24) refers to the time period from when the prior EDSS score was established (for example, a baseline EDSS score from before beginning administration of fenebrutinib or a pharmaceutically acceptable salt thereof) until the sustained increase of EDSS score is observed.

"Composite Confirmed Disability Progression" (cCDP) is a composite measure of disability progression using a combination of EDSS, 9-HPT, and T25FWT. It evaluates the progression of subject's disability over a particular time period as determined by the first occurrence of a progression event. A progression event may include any one of the following: a CDP (e.g., increase of ≥1.0 point from the baseline EDSS score in a subject with a baseline EDSS score of ≤5.5 points, or an increase of ≥0.5 point from the baseline EDSS score in a subject with a baseline EDSS score of >5.5 points); an increase of ≥20% from baseline in time to complete the 9-Hole Peg Test (9-HPT); or an increase of ≥20% from baseline in the Timed 25-Foot Walk Test (T25FWT); wherein the occurrence of the progression event is confirmed at after a specified period of time has elapsed from the initial occurrence. For example, a composite 12-week confirmed disability progression (cCDP12) refers to the occurrence of at least one progression event at an initial time point, and the same progression event is confirmed at least 12 weeks later (e.g., by re-evaluating the subject using the same test). A composite 24-week confirmed disability progression (cCDP12) refers to the occurrence of at least one progression event at an initial time period, and same progression event is confirmed at least 24 weeks later. Time to onset of a cCDP (e.g., time to onset of cCDP12 or cCDP24) refers to the time period from when the prior evaluation scores were established (for example, baseline scores before beginning administration of fenebrutinib or a pharmaceutically acceptable salt thereof) until the initial progression event is observed. Without wishing to be bound by theory, compared with endpoints based exclusively on the Expanded Disability Status Scale (EDSS), which emphasizes lower limb function, the cCDP12 requires at least one of the following: 1) an increase in EDSS score of ≥1.0 point from a baseline (BL) score of ≤5.5 points, or ≥0.5 point increase from a BL score of >5.5 points (Confirmed Disability Progression); 2) a 20% increase from BL in time to complete the 9-Hole Peg Test; 3) a 20% increase from BL in the Timed 25-Foot Walk Test. Thus, the cCDP12 is a more sensitive assessment of disability, especially at early disease stages. The use of the cCDP12 as a primary outcome may provide a clearer, more complete picture of disability progression or improvement than the EDSS alone.

"Relapse" as referred to herein includes the occurrence of a new or worsening neurological symptom or symptoms attributed to MS and immediately preceded by a relatively stable or improving neurological state of at least 30 days. In some embodiments the symptom or symptoms persist for >24 hours, and are not be attributable to a confounding clinical factor (e.g., fever, infection, injury, adverse reactions to concomitant medications). In some embodiments, the new or worsening neurological symptom or symptoms are accompanied by objective neurological worsening consistent with an increase of at least one of: a half a step (0.5 point) on the EDSS; two points on one of the selected functional systems score (FSS); or one point on two or more of the selected FSS; wherein the selected FSS are selected from the group consisting of pyramidal, ambulation, cerebellar, brainstem, sensory, or visual scores. In certain embodiments, episodic spasms, sexual dysfunction, fatigue, mood change, or bladder or bowel urgency or incontinence are not suffice to establish a relapse. In some embodiments, sexual dysfunction and fatigue need not be scored. In some embodiments, when a subject experiences a new or worsening neurological event compatible with MS representing a clinical relapse, the subject is assessed using the EDSS/FSS to determine if the event meets all relapse criteria herein described. In certain embodiments, such an EDSS evaluation is performed within 7 days from the onset of the event.

In some embodiments described herein, the response of a subject administered fenebrutinib or a pharmaceutically acceptable salt thereof may be compared to another subject who is administered a small molecule immunomodulatory agent other than fenebrutinib or a pharmaceutically acceptable salt thereof. In certain embodiments, the comparator subject is administered a small molecule immunomodulaotry agent which is not a BTK inhibitor. In certain embodiments, the comparator subject is administered a small molecule immunomodulatory agent which is an inhibitor of dihydroorotate dehydrogenase (a mitochondrial enzyme involved in de novo pyrimidine synthesis). Examples of such inhibitors of dihydroorotate dehydrogenase may include teriflunomide, or a pharmaceutically acceptable salt thereof; and leflunomide, or a pharmaceutically acceptable salt thereof. In certain embodiments, the dihydroorotate dehydrogenase is teriflunomide, or a pharmaceutically acceptable salt thereof.

II. Methods of Treatment

Provided herein are methods of treating RMS in a subject in need thereof, by administering to the subject a dose of about 200 mg fenebrutinib twice daily, or a corresponding amount of a pharmaceutically acceptable salt thereof, for a total daily dose of about 400 mg fenebrutinib, or an equivalent amount of a pharmaceutically acceptable salt thereof. Further provided is a compound for use in treating RMS in a subject in need thereof, wherein the compound is a fenebrutinib or a pharmaceutically acceptable salt thereof, and wherein the treatment comprises administering to the subject a twice daily dose of about 200 mg fenebrutinib, or a corresponding amount of a pharmaceutically acceptable salt thereof. In further embodiments, provided herein is a compound for use in the manufacture of a medicament for the treatment of RMS in a subject in need thereof, wherein the compound is fenebrutinib or a pharmaceutically acceptable salt thereof, and wherein the treatment comprises administering to the subject a twice daily dose of about 200 mg fenebrutinib, or a corresponding amount of a pharmaceutically acceptable salt thereof. In some embodiments, the treatment of RMS is evaluated using the Expanded Disability Status Scale (EDSS), the 9-Hole Peg Test (9-HPT), or the Timed 25-Foot Walk Test (T25FWT), or any combinations thereof. In some embodiments, the treatment of RMS is evaluated based the time to onset of confirmed disability progression (e.g., 12-week or 24-week CDP), or based on the time to onset of a composite confirmed disability progression (e.g., 12-week or 24-week cCDP). For example, in some embodiments, treating a subject with RMS by administering about 200 mg of fenebrutinib twice daily, or an equivalent amount of a pharmaceutically acceptable salt thereof, results in a delay in worsening of the EDSS (e.g., increase of 0.5, 1.0, 1.5, or more points compared to baseline), a delay in the worsening of the 9-HPT time (e.g., by over 20% compared to baseline), a delay in the worsening of the T25FWT time (e.g., by over 20% compared to baseline), delay to onset of CDP12, delay to onset of CDP24, delay to the onset of cCDP12, delay the onset of cCDP24, delay the onset of at least one progression event, reducing the risk of having at least one progression event, or decreasing disability in the subject. In some embodiments, treating RMS in the subject comprises reducing the annualized relapse rate of the subject. In certain embodiments, treating RMS in the subject comprises both reducing the annualized relapse rate and delaying the time to onset of cCDP12 in the subject. In other embodiments, the treatment of RMS is evaluated based on MSIS-29, Neuro-QoL Upper Extremity, PROMIS-Fatigue$_{MS}$, MSWS-12, PGI-S, WPAI: MS, PGI-C, EQ-5D-5L, C-SSRS, 9-HPT, T25FWT, EDSS, SDMT, MRI. In some embodiments, treating RMS comprises delaying the onset of disability progression, or reducing the risk of disability progression, wherein disability progression is evaluated by CDP12, cCDP12, CDP24, or cCDP24. In some embodiments, the onset is delayed, or risk reduced, by at least 15%, at least 20%, at least 25%, at least 30%, at least 35%, at least 40%, at least 45%, or at least 50%. In some embodiments, the delay or reduction is at least 15%. In some embodiments, the delay or reduction is at least 20%. In some embodiments, the delay or reduction is at least 25%. In some embodiments, the delay or reduction is at least 30%. In some embodiments, the delay or reduction is at least 35%. In some embodiments, the delay or reduction is at least 40%. In some embodiments, the delay or reduction is at least 45%. In some embodiments, the delay or reduction is at least 50%. In some embodiments, the delayed onset or reduced risk of disability progression is relative to another subject with RMS who is not administered fenebrutinib or a pharmaceutically acceptable salt thereof (or is not administered a BTK inhibitor) and is optionally administered an inhibitor of dihydroorotate dehydrogenase (such as, for example, teriflunomide or a pharmaceutically acceptable salt thereof). In certain embodiments, treating RMS comprises reducing the annualized relapse rate (ARR) in the subject, such as by at least 20%, at least 25%, at least 30%, at least 35%, at least 40%, at least 45%, or at least 50%. In some embodiments, the reduction is by at least 20%. In some embodiments, the reduction is by at least 25%. In some embodiments, the reduction is by at least 30%. In some embodiments, the reduction is by at least 35%. In some embodiments, the reduction is by at least 40%. In some embodiments, the reduction is by at least 45%. In some embodiments, the reduction is by at least 50%. In some embodiments, the reduction in ARR is relative to another subject with RMS who is not administered fenebrutinib or a pharmaceutically acceptable salt thereof (or is not administered a BTK inhibitor) and is optionally administered an inhibitor of dihydroorotate dehydrogenase (such as, for example, teriflunomide or a pharmaceutically acceptable salt thereof). In certain embodiments, treating RMS in the subject comprises both reducing the risk of disability progression (e.g., as evaluated using cCDP12) and reducing the ARR, each of which may, for example, be in comparison to another subject with RMS who is not administered fenebrutinib or a pharmaceutically acceptable salt thereof and is optionally administered an inhibitor of dihydroorotate dehydrogenase. In certain embodiments, the risk of disability progression is reduced over a period of time, for example reducing the risk of disability progression as evaluated by CDP12, cCDP12, CDP24, or cCDP24, over a period of 12 weeks, 18 weeks, 24 weeks, 36 weeks, 48 weeks, 60 weeks, 72 weeks, 84 weeks, 96 weeks, 108 weeks, or 120 weeks. In still further embodiments, the risk of CDP12 or risk of cCDP24 is reduced. In certain embodiments treating RMS in a subject in need thereof comprises reducing the number of T1 Gd+ lesions in the subject. In other embodiments, treating RMS in the subject comprises reducing the number of new and/or enlarging T2 hyperintense lesions in the subject. In certain embodiments, both the number of R1 Gd+ lesions and the number of new and/or enlarging T2 hyperintense lesions are reduced. In certain embodiments, the reduction is independently over 12 weeks, 24 weeks, 48 weeks, or 96 weeks, or any combinations thereof, after beginning administration of fenebrutinib or a pharmaceutically acceptable salt thereof. In some embodiments, the reduction is annualized, e.g., over 52 weeks. In certain embodiments, the number of R1 Gd+ lesions is reduced by at least 20%, at least 25%, at least 30%, at least 35%, at least 40%, at least 45%, or at least 50%. In some embodiments, the number of new and/or enlarging T2 hyperintense lesions is reduced by at least 20%, at least 25%, at least 30%, at least 35%, at least 40%, at least 45%, or at least 50%. In some embodiments, the reduction is by at least 20%. In some embodiments, the reduction is by at least 25%. In some embodiments, the reduction is by at least 30%. In some embodiments, the reduction is by at least 35%. In some embodiments, the reduction is by at least 40%. In some embodiments, the reduction is by at least 45%. In some embodiments, the reduction is by at least 50%. In some embodiments, the reduction of lesions is relative to another subject with RMS who is not administered fenebrutinib or a pharmaceutically acceptable salt thereof (or is not administered a BTK inhibitor) and is optionally administered an inhibitor of dihydroorotate dehydrogenase (such as, for example, teriflunomide or a pharmaceutically acceptable salt thereof).

In some embodiments, provided herein is a method of treating RMS in a subject in need thereof, by administering to the subject a dose of about 200 mg fenebrutinib twice daily, or a corresponding amount of a pharmaceutically acceptable salt thereof, for a total daily dose of about 400 mg fenebrutinib, or an equivalent amount of a pharmaceutically acceptable salt thereof. Further provided is a compound for use in treating RMS in a subject in need thereof, wherein the compound is a fenebrutinib or a pharmaceutically acceptable salt thereof, and wherein the treatment comprises administering to the subject a twice daily dose of about 200 mg fenebrutinib, or a corresponding amount of a pharmaceutically acceptable salt thereof. In further embodiments, provided herein is a compound for use in the manufacture of a medicament for the treatment of RMS in a subject in need thereof, wherein the compound is fenebrutinib or a pharmaceutically acceptable salt thereof, and wherein the treatment comprises administering to the subject a twice daily dose of about 200 mg fenebrutinib, or a corresponding amount of a pharmaceutically acceptable salt thereof. In some such embodiments, treating RMS in the subject comprises both reducing the risk of disability progression (e.g., as evaluated using cCDP12) and reducing the ARR, each of which may, for example, be in comparison to another subject with RMS who is not administered fenebrutinib or a pharmaceutically acceptable salt thereof and is optionally administered an inhibitor of dihydroorotate dehydrogenase. In some embodiments, treating RMS in the individual comprises reducing the risk of cCDP12, or increasing the time to cCDP12, by at least 20%, by at least 25%, by at least 30%, by at least 35%, by at least 40%, or by at least 45%; in combination with reducing the ARR, or relatively reducing ARR, by at least 20%, by at least 25%, by at least 30%, by at least 35%, by at least 40%, or by at least 45%. For example, reducing the risk of cCDP12 by at least 30% and reducing ARR by at least 30%. Or reducing the risk of cCDP12 by at least 35% and reducing ARR by at least 35%. Or reducing the risk of cCDP12 by at least 40% and reducing ARR by at least 40%. Or reducing the risk of cCDP12 by at least 45% and reducing ARR by at least 45%. In some embodiments, treating RMS is the individual comprises increasing the time to onset of cCDP12, alone or in combination with reducing ARR. In some embodiments, time to onset of cCDP12 is increased by at least 15%. In some embodiments, time to onset of cCDP12 is increased by at least 20%. In some embodiments, time to onset of cCDP12 is increased by at least 25%. In some embodiments, time to onset of cCDP12 is increased by at least 30%. In still further embodiments, time to onset of cCDP12 is increased by at least 35%. In still further embodiments, such as in combination with other embodiments, there is further a reduction of T1Gd+ lesions by at least 25%, at least 30%, at least 35%, at least 40%, or at least 45%. In some embodiments the T1Gd+ lesions are reduced relative to another subject not administered fenebrutinib or pharmaceutically acceptable salt thereof. In still further embodiments, there is a risk reduction cCDP24 of at least 30%, at least 35%, at least 40%, at least 45%, or at least 50%. In some embodiments, there is a risk reduction of CDP12 (e.g., EDSS) of at least 30%, at least 35%, at least 40%, at least 45%, or at least 50%. In still further embodiments, there is a reduction of mean number of new and/or enlarging T2 hyperintense lesions by at least 30%, at least 35%, at least 40%, at least 45%, or at least 50%, such as relative to another subject not administered fenebrutinib or a pharmaceutically acceptable salt thereof.

In other embodiments, provided herein is a method of reducing the annualized relapse rate in a subject with relapsing multiple sclerosis (RMS) in need thereof, the method comprising administering to the subject about 200 mg fenebrutinib twice per day, or an equivalent amount of a pharmaceutically acceptable salt thereof. Further provided is a compound for use in reducing the annualized relapse rate in a subject with relapsing multiple sclerosis (RMS) in need thereof, wherein the compound is fenebrutinib or a pharmaceutically acceptable salt thereof, and wherein the subject is administered about 200 mg fenebrutinib twice per day, or an equivalent amount of a pharmaceutically acceptable salt thereof. Also provided is a compound for use in manufacturing a medicament for use in reducing the annualized relapse rate in a subject with RMS in need thereof, wherein the compound is fenebrutinib or a pharmaceutically acceptable salt thereof, and wherein the subject is administered about 200 mg fenebrutinib twice per day, or an equivalent amount of a pharmaceutically acceptable salt thereof. In some embodiments, the annualized relapse rate (ARR) is reduced by at least 20%, at least 25%, at least 30%, at least 35%, at least 40%, at least 45%, or at least 50%. In some embodiments, the ARR is reduced by at least 20%. In some embodiments, the ARR is reduced by at least 25%. In some embodiments, the ARR is reduced by at least 30%. In some embodiments, the ARR is reduced by at least 35%. In some embodiments, the ARR is reduced by at least 40%. In some embodiments, the ARR is reduced by at least 45%. In some embodiments, the ARR is reduced by at least 50%. In certain embodiments, the ARR of the subject is reduced relative to another subject (e.g., comparator subject) with RMS who is not administered fenebrutinib or a pharmaceutically acceptable salt thereof, or who is not administered a BTK inhibitor. In certain embodiments, the comparator subject is administered an inhibitor of dihydroorotate dehydrogenase (such as, for example, teriflunomide or a pharmaceutically acceptable salt thereof). In certain embodiments, the method of reducing ARR in a subject further comprises reducing the time to onset of cCDP12, or reducing the risk of cCDP12, such as by at least 20%, at least 25%, at least 30%, at least 35%, at least 40%, at least 45%, or at least 50%.

Further provided herein is a method of reducing the risk of progression in a subject with RMS, comprising administering to the subject about 200 mg fenebrutinib twice daily, or an equivalent amount of a pharmaceutically acceptable salt thereof. Also provided is a compound for use in reducing the risk of progression in a subject with RMS, wherein the compound is fenebrutinib or a pharmaceutically acceptable salt thereof, wherein the subject is administered about 200 mg fenebrutinib twice daily, or an equivalent amount of a pharmaceutically acceptable salt thereof. In still further embodiments provided is a compound for use in the manufacture of a medicament for reducing the risk of progression in a subject with RMS, wherein the compound is fenebrutinib or a pharmaceutically acceptable salt thereof, wherein the subject is administered about 200 mg fenebrutinib twice daily, or an equivalent amount of a pharmaceutically acceptable salt thereof. Further provided herein is a method of delaying progression in a subject with RMS, comprising administering to the subject about 200 mg fenebrutinib twice daily, or an equivalent amount of a pharmaceutically acceptable salt thereof. Also provided is a compound for use in delaying progression in a subject with RMS, wherein the compound is fenebrutinib or a pharmaceutically acceptable salt thereof, wherein the subject is administered about 200 mg fenebrutinib twice daily, or an equivalent amount of a pharmaceutically acceptable salt thereof. In still further embodiments provided is a compound for use in the manufacture of a medicament for delaying progression in a subject with RMS, wherein the compound is fenebrutinib or a pharmaceutically acceptable salt thereof, wherein the subject is administered about 200 mg fenebrutinib twice daily, or an equivalent amount of a pharmaceutically acceptable salt thereof. In some embodiments, progression is evaluated using cCDP12 (e.g., an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points; or an increase from baseline of at least 20% in time to complete the 9-HPT; or increase from baseline of at least 20% in T25FWT; and wherein the change from baseline is confirmed at least 12 weeks after the initial increase). In some embodiments, progression is evaluated using CDP12 (e.g., an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points; wherein the increase is confirmed at least 12 weeks after the initial increase). In still further embodiments, progression is evaluated using CDP24, or cCDP24. In certain embodiments, the risk of progression is reduced by at least 20%, at least 25%, at least 30%, at least 35%, at least 40%, at least 45%, or at least 50%. In some embodiments, the reduction is by at least 20%. In some embodiments, the reduction is by at least 25%. In some embodiments, the reduction is by at least 30%. In some embodiments, the reduction is by at least 35%. In some embodiments, the reduction is by at least 40%. In some embodiments, the reduction is by at least 45%. In certain embodiments, the progression is delayed by at least 20%, at least 25%, at least 30%, at least 35%, at least 40%, at least 45%, or at least 50%. In some embodiments, the reduction is by at least 20%. In some embodiments, the progression is delayed by at least 25%. In some embodiments, the progression is delayed by at least 30%. In some embodiments, the progression is delayed by at least 35%. In some embodiments, the progression is delayed by at least 40%. In some embodiments, the progression is delayed by at least 45%. In some embodiments, the progression is delayed by at least 50%. In certain embodiments, the reduction of risk is over a period of 12 weeks, 18 weeks, 24 weeks, 36 weeks, 48 weeks, 60 weeks, 72 weeks, 84 weeks, 96 weeks, 108 weeks, or 120 weeks. In certain embodiments, this period of time begins just before beginning administration of fenebrutinib or a pharmaceutically acceptable salt thereof. In still further embodiments, the risk of progression is reduced, or the onset of progression is delayed, relative to another subject (e.g., comparator subject) with RMS who is not administered fenebrutinib or a pharmaceutically acceptable salt thereof, or who is not administered a BTK inhibitor. In certain embodiments, the comparator subject is administered an inhibitor of dihydroorotate dehydrogenase (such as, for example, teriflunomide or a pharmaceutically acceptable salt thereof).

In further embodiments, provided herein is a method of reducing Annualized Relapse Rate (ARR) and reducing the risk of experiencing cCDP12 in a subject with RMS, comprising administering to the subject about 200 mg fenebrutinib twice daily, or an equivalent amount of a pharmaceutically acceptable salt thereof. Also provided is a compound for use in reducing Annualized Relapse Rate (ARR) and reducing the risk of experiencing cCDP12 in a subject with RMS, wherein the compound is fenebrutinib or a pharmaceutically acceptable salt thereof, wherein the subject is administered about 200 mg fenebrutinib twice daily, or an equivalent amount of a pharmaceutically acceptable salt thereof. In still further embodiments provided is a compound for use in the manufacture of a medicament for reducing Annualized Relapse Rate (ARR) and reducing the risk of experiencing cCDP12 in a subject with RMS, wherein the compound is fenebrutinib or a pharmaceutically acceptable salt thereof, wherein the subject is administered about 200 mg fenebrutinib twice daily, or an equivalent amount of a pharmaceutically acceptable salt thereof. In some embodiments, the annualized relapse rate (ARR) is reduced by at least 20%, at least 25%, at least 30%, at least 35%, at least 40%, at least 45%, or at least 50%. In certain embodiments, the risk of experiencing cCDP12 is reduced by at least 20%, at least 25%, at least 30%, at least 35%, at least 40%, at least 45%, or at least 50%. In some embodiments, the ARR is reduced by at least 20%, and the risk of experiencing cCDP12 is reduced by at least 20%. In some embodiments, the ARR is reduced by at least 25%, and the risk of experiencing cCDP12 is reduced by at least 25%. In some embodiments, the ARR is reduced by at least 30%, and the risk of experiencing cCDP12 is reduced by at least 30%. In some embodiments, the ARR is reduced by at least 35%, and the risk of experiencing cCDP12 is reduced by at least 35%. In some embodiments, the ARR is reduced by at least 40%, and the risk of experiencing cCDP12 is reduced by at least 40%. In some embodiments, the ARR is reduced by at least 45%, and the risk of experiencing cCDP12 is reduced by at least 45%. In some embodiments, the ARR is reduced by at least 50%, and the risk of experiencing cCDP12 is reduced by at least 50%. In certain embodiments, reduction of the risk of experiencing cCDP12 comprises reduction in the risk of experiencing one or more of: (i) an increase from baseline in Expanded Disability Status Scale (EDSS) score of 1.0 point in patients with a baseline EDSS score of ≤5.5 or ≥0.5 points in patients with a baseline EDSS score of >5.5 (confirmed disability progression [CDP]); (ii) ≥20% increase from baseline in timed 25-foot walk test (T25FWT); or (iii) ≥20% increase from baseline in time to complete the 9-hole peg test (9-HPT). In certain embodiments, the risk of experiencing at least two of (i)-(iii) is reduced. In some embodiments, the risk of experiencing one of (i)-(iii) is reduced. In some embodiments, the risk of experiencing two of (i)-(iii) is reduced. In still further embodiments, the risk of experiencing all three of (i)-(iii) is reduced. In certain embodiments, the ARR and the risk of experiencing cCDP12 is reduced relative to another subject (e.g., comparator subject) with RMS who is not administered fenebrutinib or a pharmaceutically acceptable salt thereof, or who is not administered a BTK inhibitor. In certain embodiments, the comparator subject is administered an inhibitor of dihydroorotate dehydrogenase (such as, for example, teriflunomide or a pharmaceutically acceptable salt thereof).

In still further embodiments, provided herein is a method of reducing the number of T1 Gd+ lesions in a subject with RMS in need thereof, comprising administering to the subject about 200 mg fenebrutinib twice daily, or an equivalent amount of a pharmaceutically acceptable salt thereof. Further provided is a method of reducing the number of new and/or enlarging T2 hyperintense lesions in a subject with RMS in need thereof, comprising administering to the subject about 200 mg fenebrutinib twice daily, or an equivalent amount of a pharmaceutically acceptable salt thereof. Also provided is a compound for use in, or a compound for use in the manufacture of a medicament for, reducing the number of T1 Gd+ lesions in a subject with RMS in need thereof, wherein the subject is administered about 200 mg fenebrutinib twice daily, or an equivalent amount of a pharmaceutically acceptable salt thereof. Further provided is a compound for use in, or a compound for use in the manufacture of a medicament for, reducing the number of new and/or enlarging T2 hyperintense lesions in a subject with RMS in need thereof, wherein the subject is administered about 200 mg fenebrutinib twice daily, or an equivalent amount of a pharmaceutically acceptable salt thereof. The number of lesions in the patient may be evaluated, for example, using MRI. In some embodiments, both the number of R1 Gd+ lesions and the number of new and/or enlarging T2 hyperintense lesions are reduced. In certain embodiments, the reduction is independently over 12 weeks, 24 weeks, 48 weeks, or 96 weeks, or any combinations thereof, after beginning administration of fenebrutinib or a pharmaceutically acceptable salt thereof. In some embodiments, the reduction is annualized, e.g., over 52 weeks. In certain embodiments, the number of R1 Gd+ lesions is reduced by at least 20%, at least 25%, at least 30%, at least 35%, at least 40%, at least 45%, or at least 50%. In some embodiments, the number of new and/or enlarging T2 hyperintense lesions is reduced by at least 20%, at least 25%, at least 30%, at least 35%, at least 40%, at least 45%, or at least 50%. In some embodiments, the reduction is by at least 20%. In some embodiments, the reduction is by at least 25%. In some embodiments, the reduction is by at least 30%. In some embodiments, the reduction is by at least 35%. In some embodiments, the reduction is by at least 40%. In some embodiments, the reduction is by at least 45%. In some embodiments, the reduction is by at least 50%. In some embodiments, the reduction of lesions is relative to another subject with RMS who is not administered fenebrutinib or a pharmaceutically acceptable salt thereof (or is not administered a BTK inhibitor) and is optionally administered an inhibitor of dihydroorotate dehydrogenase (such as, for example, teriflunomide or a pharmaceutically acceptable salt thereof). Thus, for example, in some embodiments wherein the reduction is relative, the subject who is administered fenebrutinib or a pharmaceutically acceptable salt thereof may, over an evaluation period, experience a total increase in the number of R1 Gd+ lesions and/or the number of new and/or enlarging T2 hyperintense lesions (such as compared to before beginning administration), but this increase will be less than that experienced by a comparator subject. Thus, for example, provided herein are methods, compounds for use, and use of compounds in the manufacture of a medicament for, reducing in a subject with RMS the number of the number of R1 Gd+ lesions and/or the number of new and/or enlarging T2 hyperintense lesions, comprising administering to the subject about 200 mg fenebrutinib twice daily, or an equivalent amount of a pharmaceutically acceptable salt thereof, wherein the reduction is relative to another subject who is not administered fenebrutinib or a pharmaceutically acceptable salt thereof (e.g., comparator subject), and wherein the comparator subject is administered an inhibitor of dihydroorotate dehydrogenase (such as, for example, teriflunomide or a pharmaceutically acceptable salt thereof).

In still further embodiments, provided herein is a method of decreasing disability in a subject with RMS, comprising administering to the subject about 200 mg fenebrutinib twice per day, or an equivalent amount of a pharmaceutically acceptable salt thereof, for a total daily dose of about 400 mg fenebrutinib, or an equivalent amount of a pharmaceutically acceptable salt thereof. In some embodiments, provided is a compound for use in a method of decreasing disability in a subject with RMS, wherein the compound is fenebrutinib or a pharmaceutically acceptable salt thereof, and the method comprises administering to the subject about 200 mg fenebrutinib twice per day, or an equivalent amount of a pharmaceutically acceptable salt thereof. In further embodiments, provided herein is a compound for use in the manufacture of a medicament for use in a method of decreasing disability in a subject with RMS, wherein the compound is fenebrutinib or a pharmaceutically acceptable salt thereof, and wherein the method comprises administering to the subject a daily dose of about 400 mg fenebrutinib, or a corresponding amount of a pharmaceutically acceptable salt thereof. Decreasing disability may comprise reducing the psychological impact of MS; increasing upper limb function; increasing walking ability; decreasing fatigue; improving work status; or decreasing global impression of MS severity; or any combinations thereof. Decreasing disability may further include decreasing one or more symptoms of RMS, or decreasing one or more physical impacts of RMS on the subject. The decrease in disability (including, for example, one or more symptoms or physical impacts, or other aspects as described herein) may be evaluated as described herein, such as using MSIS-29, Neuro-QoL Upper Extremity, PROMIS-Fatigue$_{MS}$, MSWS-12, PGI-S, WPAI: MS, PGI-C, EQ-5D-5L, C-SSRS, 9-HPT, T25FWT, EDSS, SDMT, or MRI. In some embodiments, one or more of 9-HPT, T25FWT, or EDSS is used. In some embodiments, decreasing disability comprises a subject that can complete the T25FWT and/or 9-HPT more quickly, or a decrease in the EDSS score (e.g., closer to "normal"). In certain embodiments, a decrease in disability comprises an improvement in one or more metrics of RMS, such as one evaluated using MSIS-29, Neuro-QoL Upper Extremity, PROMIS-Fatigue$_{MS}$, MSWS-12, PGI-S, WPAI:MS, PGI-C, EQ-5D-5L, C-SSRS, 9-HPT, T25FWT, EDSS, SDMT, or MRI. In certain embodiments, the improvement is at least 5%, at least 10%, at least 15%, at least 20%, at least 25%, at least 30%, or at least 35% in at least one metric of RMS (e.g., in T25FWT time, or 9-HPT time, or EDSS score), as compared to the same metric evaluated in the same subject prior to beginning administration of fenebrutinib or a pharmaceutically acceptable salt thereof. In some embodiments, two, three, four, five or more metrics are improved, wherein each improvement level is independent (e.g., one metric improves by at least 10%, another metric improves by at least 20%). In some embodiments, the improvement is at least 5%. In some embodiments, the improvement is at least 10%. In some embodiments, the improvement is at least 15%. In some embodiments, the improvement is at least 20%. In some embodiments, the improvement is at least 25%. In some embodiments, the improvement is at least 30%. In some embodiments, the improvement is at least 35%. In some embodiments, the improvement is at least 40%. In still further embodiments, the improvement is at least 45%. In some embodiments, the improvement is compared to the same metric evaluated in the same subject within 1 week, or within 0 to 28 days, or within 6 weeks prior to beginning administration of fenebrutinib or a pharmaceutically acceptable salt thereof.

In some embodiments of the methods, compounds for use, or use of a compound as described herein, about 200 mg fenebrutinib, or a corresponding amount of a pharmaceutically acceptable salt thereof, is adminstered twice daily to a subject with RMS, wherein the subject with RMS has a diagnosis of RMS in accordance with the revised 2017 McDonald Criteria (Thompson et al. 2018; incorporated herein by reference in its entirety). In certain embodiments, the subject with RMS has a diagnosis of RMS in accordance with the revised 2017 McDonald Criteria, and has at least one of: (a) at least two documented clinical relapses within the previous 2 years or one documented clinical relapse within the previous 12 months, prior to beginning administration of fenebrutinib or pharmaceutically acceptable salt thereof; or (b) at least one T1Gd+ lesion within 12 months prior beginning administration of fenebrutinib or a pharmaceutically acceptable salt thereof. Assessment of the presence of T1Gd+ lesions may be done, for example, via MRI. In certain embodiments, the diagnosis of RMS may include a diagnosis of aSPMS. In still further embodiments, the subject with RMS is between 18-55 years of age. In some embodiments, the subject with RMS has an EDSS score of 0-5.5 prior to beginning administration of fenebrutinib, or a pharmaceutically acceptable salt thereof, such as within the previous week, or previous month. In some embodiments, the subject with RMS is neurologically stable for at least 30 days prior to beginning administration of fenebrutinib, or a pharmaceutically acceptable salt thereof. In some such embodiments, the method, compound for use, or use of a compound, is for treating RMS; reducing ARR; decreasing disability; delaying the onset of at least one progression event; reducing the risk of having at least one progression event; increasing mobility; or increasing time to onset of cCDP12; or any combination thereof, in a subject with RMS in need thereof; and comprises administering to the subject in need thereof 200 mg of fenebrutinib, or an equivalent amount of a pharmaceutically acceptable salt thereof, twice daily.

In some embodiments of the methods, compounds for use, or use of a compound as described herein, about 200 mg fenebrutinib, or a corresponding amount of a pharmaceutically acceptable salt thereof, is adminstered twice daily to a subject with RMS, wherein the subject with RMS does not have a disease duration of greater than 10 years from the onset of symptoms in combination with an EDSS score of less than 2.0 prior to beginning administration of fenebrutinib or pharmaceutically acceptable salt thereof. In some embodiments, the subject with RMS does not have a diagnosis of PPMS or non-active SPMS. In some embodiments, the subject with RMS does not have progressive multifocal leukoencephalopathy, or does not have a history of progressive multifocal leukoencephalopathy. In certain embodiments, the subject with RMS does not have a history of cancer within 10 years prior to beginning administration of fenebrutinib, or a pharmaceutically acceptable salt thereof. In certain embodiments, the subject with RMS has not had a hematological malignancy or solid tumor within 10 years prior to beginning administration of fenebrutinib, or a pharmaceutically acceptable salt thereof. In still further embodiments, the subject with RMS does not have any other neurological disorders. Such other neurological disorders may include, for example, a history of an ischemic cerebrovascular disorder (e.g., stroke, transient ischemic attack, spontaneous intracranial hemorrhage, or traumatic intracranial hemorrhage) or ischemia of the spinal cord; history or known presence of a CNS or spinal cord tumor (e.g., meningioma or glioma); history or known presence of potential metabolic causes of myelopathy (e.g., untreated vitamin B12 deficiency); history or known presence of infectious causes of myelopathy (e.g., syphilis, Lyme disease, HTLV-1, herpes zoster myelopathy); history of genetically inherited progressive CNS degenerative disorder (e.g., hereditary paraparesis, mitochondrial myopathy, encephalopathy, lactic acidosis, stroke syndrome); neuromyelitis optica spectrum disorder; history or known presence of systemic autoimmune disorders potentially causing progressive neurological disease (e.g., lupus, anti-phospholipid antibody syndrome, Sjögren syndrome, Behçet disease); history or known presence of sarcoidosis; or history of severe, clinically significant brain or spinal cord trauma (e.g., cerebral contusion, spinal cord compression). In some embodiments, the subject with RMS does not have evidence of clinically significant psychiatric, pulmonary, renal, hepatic (including Gilbert syndrome), metabolic, gastrointestinal (GI), or cardiovascular disease (including arrhythmias or QTc prolongation), or endocrine disease (including uncontrolled diabetes, non-gallstone pancreatitis, or chronic pancreatitis). In some embodiments, the subject with RMS does not have heart disease. In certain embodiments, the subject with RMS does not have congestive heart failure. Congestive heart failure may be evaluated, for example, using the New York Heart Association criteria. In certain embodiments, the subject with RMS does not meet the Class III or Class IV criteria for congestive heart failure as described by the New York Heart Association. In still further embodiments, the subject with RMS does not have a history of ventricular dysrhythmias or risk factors for ventricular dysrhythmias such as long QT syndrome or other genetic risk factors (e.g., Brugada syndrome); structural heart disease; coronary heart disease (symptomatic or with ischemia demonstrated by diagnostic testing, prior coronary artery bypass grafting, or coronary lesions>70% diameter stenosis that have not been or cannot be re-vascularized); clinically significant electrolyte abnormalities (e.g., hypokalemia, hypomagnesemia, hypocalcemia); family history of sudden, unexplained death; or cardiac ion channel genetic mutations (e.g., congenital long QT syndrome). In some embodiments, the subject with RMS does not have a hereditary galactose intolerance, total lactase deficiency, or glucose-galactose malabsorption. In some embodiments, the subject with RMS does not have hypoproteinemia (e.g., in case of severe liver disease or nephrotic syndrome) with serum albumin<<3.0 g/dL. In some embodiments, the subject with RMS does not have severe renal impairment undergoing dialysis and/or estimated glomerular filtration rate (eGFR)<60 m/min/1.73

$m^2$. In some embodiments, the subject with RMS has a glomerular filtration rate of ≥60 m/min/1.73 $m^2$. In some embodiments, the subject with RMS does not have severe hepatic disease impairment, such as Child-Pugh Class C impairment. In still further embodiments, the subject with RMS does not have one or more of: ALT or AST>2×upper limit of normal (ULN); total bilirubin greater than 1.5×ULN, with the exception of a subject with Gilbert syndrome; or persisting elevations of serum amylase or lipase greater than 2×ULN. In certain embodiments, the subject with RMS does not have either: (a) significantly impaired bone marrow function or significant anemia, leukopenia, neutropenia or thrombocytopenia; or (b) any of hemoglobin<9.5 g/dL, absolute white cell count<4000 cells/$mm^3$ (μL), platelet count<100 cells×$10^9$/L, or absolute neutrophil≤1500 cells/$mm^3$ (μL); or any combinations of (a) and (b). In still further embodiments, the subject with RMS does not have any concomitant disease that may require chronic treatment with systemic corticosteroids or immunosuppressants while being administered fenebrutinib or a pharmaceutically acceptable salt thereof. In still further embodiments, the subject with RMS does not have a positive test for active, latent, or inadequately treated hepatitis B; or a positive test for hepatitis C; or evidence of active or latent or inadequately treated infection with tuberculosis (TB), or any combinations thereof, before beginning administration of fenebrutinib or a pharmaceutically acceptable salt thereof. In other embodiments, the subject with RMS does not have any abnormalities in hepatic synthetic function tests, such as PT, INR, or aPTT. In still further embodiments, the subject with RMS does not have one or more of: a history of hospitalization or transfusion for a GI bleed; or a known bleeding diathesis; or any condition possibly affecting oral drug absorption; or a history of or currently active primary or secondary (non-drug-related) immunodeficiency, including known history of HIV infection; or IgG<500 mg/dL; or contraindication for MRI scans; or contraindication for gadolinium administration; or previous history of transplantation or anti-rejection therapy. In still further embodiments, the subject with RMS does is not concomitantly administered an adrenocorticotropic hormone or systemic corticosteroid, or not administered adrenocorticotropic hormone or systemic corticosteroid within 4 weeks of beginning administration of fenebrutinib or a pharmaceutically acceptable salt thereof. In still further embodiments, the subject with RMS has not been administered IV Ig or plasmapheresis within 12 weeks prior to beginning administration of fenebrutinib or a pharmaceutically acceptable salt thereof. In still further embodiments, the subject with RMS has not previously been administered another BTK inhibitor. In yet other embodiments, before beginning administration of fenebrutinib or a pharmaceutically acceptable salt thereof, the subject with RMS has not been administered: a strong CYP3A4 inhibitor, or a strong or moderate CYP3A4 inducer, within 7 days or 5 drug elimination half-lives (whichever is longer); a CYP3A4 substrate with a narrow therapeutic window within 7 days or 5 drug elimination half-lives (whichever is longer); an anti-CD20 within 6 months, or optionally within 2 years; fingolimod, siponimod, or ozanimod within 8 weeks; natalizumab within 6 months, if natalzimuab was administered for more than one year; mycophenolate mofetil or methotrexate within 12 weeks; teriflunomide within the last 24 months, unless teriflunomide plasma concentrations are <0.02 mg/L; or cladribine, mitoxantrone, daclizumab, alemtuzumab, or cyclophosphamide. In still further embodiments, the subject with RMS, while being administered fenebrutinib or a pharmaceutically acceptable salt thereof, is not concomitantly administered any one or more of: a strong CYP3A4 inhibitor; a strong or moderate CYP3A4 inducer; or a CYP3A4 substrate with a narrow therapeutic window. Examples of strong CYP3A4 inhibitors include boceprevir, cobicistat, clarithromycin, danoprevir/ritonavir, elvitegravir/ritonavir, indinavir/ritonavir, itraconazole, idelalisib, ketoconazole, lopinavir/ritonavir, nefazodone, nelfinavir, posaconazole, ritonavir, saquinavir, telaprevir, telithromycin, and voriconazole. Examples of strong CYP3A inducers include apalutamide, carbamazepine, enzalutamide, mitotane, phenytoin, rifampin, and hyperforin (St. John's Wort). Examples of moderate CYP3A inducers include bosentan, dexamethasone, efavirenz, etravirine, phenobarbital, primidone, phenobarbital, and rifabutin. Examples of CYP3A4 substrates with a narrow therapeutic window include alfentanil, astemizole, cyclosporine, cisapride, dihydroergotamine, ergotamine, everolimus, fentanyl, pimozide, quinidine, sirolimus, terfenadine, and tacrolimus. In some such embodiments, the method, compound for use, or use of a compound, is for treating RMS; reducing ARR; decreasing disability; delaying the onset of at least one progression event; reducing the risk of having at least one progression event; increasing mobility; or increasing time to onset of cCDP12; or any combinations thereof, in a subject with RMS in need thereof; and comprises administering to the subject in need thereof 200 mg of fenebrutinib, or an equivalent amount of a pharmaceutically acceptable salt thereof, twice daily.

As described above, fenebrutinib is a BTK inhibitor that binds non-covalently and reversibly to BTK. As demonstrated in Example 4, fenebrutinib exhibits high selectivity and high potency, which may be associated with fewer off-target adverse events and an improved RMS therapeutic index compared with less selective BTK inhibitors. Further, the long residence time may also improve the MS therapeutic index by mimicking the advantage of covalent inhibition without the risk of immunogenic hapten formation that covalent BTK inhibitors may carry. Fenebrutinib may have a dual mechanism of action by inhibiting the activation of both B cells and myeloid lineage progenitor cells, and in vitro studies have shown fenebrutinib to inhibit said cells with higher potency than other BTK inhibitors (Example 4). Further, as illustrated in Example 5, there is a large safety database around fenebrutinib from previous clinical studies in autoimmune disorders other than MS, which demonstrate that fenebrutinib is safe and well-tolerated, and potential BTK-class side effects may be less relevant to fenebrutinib compared to other BTK inhibitors, possibly due to its higher selectivity. The noncovalent binding, reversible mechanism, and greater selectivity of fenebrutinib may result in a more favorable safety profile compared to other BTK inhibitors, in the treatment of RMS.

III. Pharmaceutical Compositions and Formulations

Also provided herein are pharmaceutical compositions and formulations comprising fenebrutinib, or a pharmaceutically acceptable salt thereof, for use in the methods of treatment described herein (e.g., treating RMS, etc.). In some embodiments, the pharmaceutical compositions and formulations further comprise one or more pharmaceutically acceptable carriers. WO 2017/148837, which is hereby incorporated by reference in its entirety, discloses formulations and dosage forms comprising fenebrutinib and pharmaceutically acceptable salts thereof. In some embodiments, a formulation described in WO 2017/148837 is used to deliver fenebrutinib to a subject according to one or more of the methods provided herein.

Fenebrutinib, or a pharmaceutically acceptable salt thereof can be administered by any suitable means, including oral, parenteral, intrapulmonary, and intranasal, and, if desired for local treatment, intralesional administration. In certain embodiments, oral administration is used.

Pharmaceutically acceptable salts of fenebrutinib may be used in the methods herein. As used herein, the term "pharmaceutically acceptable salt" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

In some of the embodiments provided herein, an oral dose of fenebrutinib, or a pharmaceutically acceptable salt thereof, is administered as one or more tablets or capsules. For example, in some embodiments, about 200 mg of fenebrutinib, or an equivalent amount of a pharmaceutically acceptable salt thereof, is administered twice daily as one or more tablets, such as one, two, three, four, five, or six tablets administered twice daily. In other embodiments, about 200 mg of fenebrutinib, or an equivalent amount of a pharmaceutically acceptable salt thereof, is administered twice daily as one or more capsules, such as one, two, three, four, five, or six capsules administered twice daily. Such capsules or tablets may contain, in some embodiments, about 50 mg, about 75 mg, about 100 mg, about 125 mg, about 150 mg, about 175, mg, about 200 mg, or about 225 mg each of fenebrutinib, or an equivalent amount of a pharmaceutically acceptable salt thereof. For example, in certain embodiments, about 200 mg is administered twice daily to a subject in need thereof, wherein each 200 mg dose is administered as one capsule comprising about 200 mg fenebrutinib, or an equivalent amount of a pharmaceutically acceptable salt thereof; or each 200 mg dose is administered as two capsules comprising about 100 mg fenebrutinib, or an equivalent amount of a pharmaceutically acceptable salt thereof. In certain embodiments, about 200 mg of fenebrutinib is administered twice daily (e.g., about 400 mg total daily), wherein each 200 mg is administered as two capsules comprising about 100 mg fenebrutinib. In other embodiments, about 200 mg is administered twice daily to a subject in need thereof, wherein each 200 mg dose is administered as one tablet comprising about 200 mg fenebrutinib, or an equivalent amount of a pharmaceutically acceptable salt thereof; or each 200 mg dose is administered as two tablets comprising about 100 mg fenebrutinib, or an equivalent amount of a pharmaceutically acceptable salt thereof. In certain embodiments, about 200 mg of fenebrutinib is administered twice daily (e.g., about 400 mg total daily), wherein each 200 mg is administered as two tablets comprising about 100 mg fenebrutinib. Thus, in some embodiments, the daily dose of fenebrutinib is about 400 mg daily, such as from about 360 mg to about 440 mg daily, or an equivalent amount of a pharmaceutically acceptable salt of fenebrutinib. In certain embodiments, 400 mg of fenebrutinib is administered daily.

In further embodiments as provided herein, an article of manufacture or a kit is provided comprising fenebrutinib, or a pharmaceutically acceptable salt thereof, and a container. In certain embodiments, further include is a package insert comprising instructions for using fenebrutinib, or a pharmaceutically acceptable salt thereof. Suitable containers for kits include, for example, a bottle, a box, a blister pack, or a combinations thereof (e.g., a blister pack in a box). In some embodiments, the container holds the formulation and the label on, or associated with, the container may indicate directions for use. The article of manufacture or kit may further include other materials desirable from a commercial and user standpoint, including package inserts with instructions for use.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

Enumerated Embodiments

Embodiment 1. A method of treating relapsing multiple sclerosis (RMS) in a subject in need thereof, comprising administering to the subject about 200 mg fenebrutinib twice daily, or an equivalent amount of a pharmaceutically acceptable salt thereof.

Embodiment 2. A method of reducing Annualized Relapse Rate (ARR) and reducing the risk of experiencing cCDP12 in a subject with RMS, comprising administering to the subject about 200 mg fenebrutinib twice daily, or an equivalent amount of a pharmaceutically acceptable salt thereof.

Embodiment 3. The method of embodiment 1 or 2, comprising evaluating the onset of composite 12-week confirmed disability progression (cCDP12), wherein onset of cCDP12 comprises at least one of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; or (c) increase from baseline of at least 20% in T25FWT;

and wherein the change from baseline is confirmed at least 12 weeks after the initial increase.

Embodiment 4. The method of any one of embodiments 1 to 3, wherein time to onset of cCDP12 in the subject is increased.

Embodiment 5. The method of any one of embodiments 1 to 4, wherein the risk of cCDP12 in the subject is reduced, and the annualized relapse rate of the subject is reduced, after beginning administration of fenebrutinib or a pharmaceutically acceptable salt thereof; wherein the risk reduction and annualized relapse rate reduction are independently greater than 25%.

Embodiment 6. A method of reducing the Annualized Relapse Rate (ARR) in a subject with relapsing multiple sclerosis (RMS) in need thereof, the method comprising administering to the subject about 200 mg fenebrutinib twice per day, or an equivalent amount of a pharmaceutically acceptable salt thereof.

Embodiment 7. The method of embodiment 6, wherein the reduction of annualized relapse rate is greater than 25%.

Embodiment 8. The method of any one of embodiments 2 to 7, wherein the reduction is relative to another subject with RMS who is not administered fenebrutinib or a pharmaceutically acceptable salt thereof, and who is optionally administered a small molecule inhibitor of dihydroorotate dehydrogenase.

Embodiment 9. The method of any one of embodiments 1 to 8, wherein the fenebrutinib or pharmaceutically acceptable salt thereof is administered orally.

Embodiment 10. The method of any one of embodiments 1 to 9, wherein the fenebrutinib or pharmaceutically acceptable salt thereof is administered in the form of one or more tablets or capsules.

Embodiment 11. The method of any one of embodiments 1 to 10, wherein the fenebrutinib or pharmaceutically acceptable salt thereof is administered in the form of two tablets twice daily, each tablet comprising about 100 mg fenebrutinib or an equivalent amount of a pharmaceutically acceptable salt thereof.

Embodiment 12. The method of any one of embodiments 1 to 11, wherein the free form of fenebrutinib is administered.

Embodiment 13. A compound for use in the treatment of relapsing multiple sclerosis (RMS) in a subject in need thereof, wherein the compound is fenebrutinib or a pharmaceutically acceptable salt thereof, and wherein the treatment comprises administering to the subject about 200 mg fenebrutinib twice daily, or an equivalent amount of a pharmaceutically acceptable salt thereof.

Embodiment 14. A compound for use in reducing Annualized Relapse Rate (ARR) and reducing the risk of experiencing cCDP12 in a subject with RMS, wherein the compound is fenebrutinib or a pharmaceutically acceptable salt thereof, and wherein reducing ARR and reducing the risk of experiencing cCDP12 comprises administering to the subject about 200 mg fenebrutinib twice daily, or an equivalent amount of a pharmaceutically acceptable salt thereof.

Embodiment 15. The compound for use of embodiment 13 or 14, further comprising evaluating the onset of composite 12-week confirmed disability progression (cCDP12), wherein onset of cCDP12 comprises at least one of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; or (c) increase from baseline of at least 20% in T25FWT;

and wherein the change from baseline is confirmed at least 12 weeks after the initial increase.

Embodiment 16. The compound for use of any one of embodiments 13 to 15, wherein time to onset of cCDP12 in the subject is increased.

Embodiment 17. The compound for use of any one of embodiments 13 to 16, wherein the risk of cCDP12 in the subject is reduced, and the annualized relapse rate of the subject is reduced, after beginning administration of fenebrutinib or a pharmaceutically acceptable salt thereof; wherein the risk reduction and annualized relapse rate reduction are independently greater than 25%.

Embodiment 18. A compound for use in reducing the annualized relapse rate in a subject with relapsing multiple sclerosis (RMS) in need thereof, wherein the compound is fenebrutinib or a pharmaceutically acceptable salt thereof, and wherein the reduction comprises administering to the subject about 200 mg fenebrutinib twice per day, or an equivalent amount of a pharmaceutically acceptable salt thereof.

Embodiment 19. The compound for use of embodiment 18, wherein the reduction of annualized relapse rate is greater than 25%.

Embodiment 20. The compound for use of any one of embodiments 13 to 19, wherein the reduction is relative to another subject with RMS who is not administered fenebrutinib or a pharmaceutically acceptable salt thereof, and who is optionally administered a small molecule inhibitor of dihydroorotate dehydrogenase.

Embodiment 21. The compound for use of any one of embodiments 13 to 20, wherein the fenebrutinib or pharmaceutically acceptable salt thereof is administered orally.

Embodiment 22. The compound for use of any one of embodiments 13 to 21, wherein the fenebrutinib or pharmaceutically acceptable salt thereof is administered in the form of one or more tablets or capsules.

Embodiment 23. The compound for use of any one of embodiments 13 to 22, wherein the fenebrutinib or pharmaceutically acceptable salt thereof is administered in the form of two tablets twice daily, each tablet comprising about 100 mg fenebrutinib or an equivalent amount of a pharmaceutically acceptable salt thereof.

Embodiment 24. The compound for use of any one of embodiments 13 to 23, wherein the compound is the free form of fenebrutinib.

EXAMPLES

The present disclosure will be more fully understood by reference to the following examples. They should not, however, be construed as limiting the scope of the invention.

It is understood that the examples and embodiments described herein are for illustrative purposes only and that various modifications or changes in light thereof will be suggested to persons skilled in the art and are to be included within the spirit and purview of this application and scope of the appended claims.

Example 1: A Phase III Multicenter, Randomized, Double-Blind, Double-Dummy, Parallel-Group Study to Evaluate the Efficacy and Safety of Fenebrutinib in Adults with Relapsing Multiple Sclerosis This Phase III study will evaluate the efficacy, safety, and pharmacokinetics of fenebrutinib compared with teriflunomide in patients with relapsing multiple sclerosis (RMS). Specific objectives and corresponding endpoints for the study are outlined below.

Primary Efficacy Objective

The primary efficacy objective for this study is to evaluate the efficacy of fenebrutinib compared with teriflunomide on the basis of the following co-primary endpoint:

- Time to onset of composite 12-week confirmed disability progression (cCDP12) defined as the first occurrence of a progression according to at least one of the following three criteria:
  - An increase from baseline in Expanded Disability Status Scale (EDSS) score of ≥1.0 point in patients with a baseline EDSS score of ≤5.5 or ≥0.5 points in patients with a baseline EDSS score of >5.5 (confirmed disability progression [CDP])
  - ≥20% increase from baseline in timed 25-foot walk test (T25FWT)
  - ≥20% increase from baseline in time to complete the 9-hole peg test (9-HPT)
- Annualized protocol-defined relapse rate Secondary Efficacy Objective The secondary efficacy objective for this study is to evaluate the effectiveness of fenebrutinib treatment compared with teriflunomide on the basis of the following endpoints:

- Time to onset of composite 24-week confirmed disability progression (cCDP24)
- Time to onset of 12-week CDP (CDP12), defined as an increase from baseline in EDSS score of ≥1.0 point in patients with a baseline EDSS score of ≤5.5 or ≥0.5 points in patients with a baseline EDSS score of >5.5 (CDP)
- Time to onset of 24-week CDP (CDP24)
- Total number of T1-weighted gadolinium (Gd)-enhancing lesions as detected by brain magnetic resonance imaging (MRI)
- Total number of new and/or enlarging T2-weighted lesions as detected by brain MRI
- Percentage change in total brain volume from Week 24 to Week 96 as detected by brain MRI
- Change from baseline in patient reported physical impacts of multiple sclerosis (MS) (as measured by Multiple Sclerosis Impact Scale [MSIS]-29 physical scale) at Week 96
- Time to 4-point worsening in the Symbol Digit Modality Test (SDMT) score Exploratory Efficacy Objectives The exploratory efficacy objective for this study is to evaluate the efficacy of fenebrutinib compared with teriflunomide may include, but are not limited to, the following endpoints:

- Proportion of patients with worsening in SDMT by 4 points
- Change from baseline and proportion of patients with a meaningful deterioration from baseline at Week 120 for the following patient-reported outcomes (PROs):
  - Psychological impacts of MS (MSIS-29 psychological scale)
  - Upper limb function (Quality of life in neurological disorders Upper Extremity Function Form)
  - Walking (Multiple Sclerosis Walking Scale, 12-Item [MSWS-12])
  - Fatigue (Patient-Reported Outcomes Measurement Information System Fatigue Short form for Multiple Sclerosis)
  - Work Status (Work Productivity Activity Index: MS v2.0)
  - Global impression of MS Severity (Patient Global Impression of Severity)
- Time to ≥20% increase in 12-week confirmed 9-HPT
- Time to ≥20% increase in 12-week confirmed T25FWT
- Time to ≥20% increase in 24-week confirmed T25FWT
- Time to ≥20% increase in 24-week confirmed 9-HPT
- Total number of new T1-hypo-intense lesions (black holes) from the baseline as detected by brain MRI
- Proportion of patients who are relapse free
- Proportion of patients with a meaningful deterioration from baseline in patient-reported physical impacts of MS (MSIS-29 physical scale) at Week 96
- Proportion of patients with a meaningful deterioration from baseline in patient-reported psychological impacts of MS (MSIS-29 psychological scale) at Week 96
- Proportion of patients free of disability progression (cCDP12, cCDP24, CDP12, and CDP24) at Week 96 and at the time of clinical cutoff of primary analysis Safety Objectives The safety objective for this study is to evaluate the safety of fenebrutinib compared with teriflunomide on the basis of the following endpoints:

- The nature, frequency, timing, and severity of adverse events; serious adverse events; and adverse events leading to study treatment withdrawal
- Change from baseline in targeted vital signs
- Change from baseline in targeted ECG parameters
- Change from baseline in clinical laboratory results following study treatment administration
- Change from baseline in the Columbia-Suicide Severity Rating Scale (C-SSRS)

Pharmacokinetic Objective

The pharmacokinetic (PK) objective for this study is to characterize the fenebrutinib PK profile on the basis of the following endpoint:

- Plasma concentration of fenebrutinib at specified time points

Sparse PK samples will be collected in all patients. However, to better characterize fenebrutinib pharmacokinetics in patients with MS, more intensive PK samples will be collected in a small subset of patients.

The exploratory PK objectives for this study are as follows:

- To evaluate potential relationships between drug exposure and the efficacy and safety of fenebrutinib on the basis of the following endpoints:
  - Relationship between plasma concentrations of fenebrutinib and efficacy endpoints
  - Relationship between plasma concentrations of fenebrutinib and safety endpoints To evaluate potential relationships between selected covariates and exposure to fenebrutinib on the basis of the following endpoint:

Relationship between selected covariates and plasma concentrations of fenebrutinib Biomarker Objective The exploratory biomarker objective for this study is to identify and/or evaluate biomarkers that are predictive of response to fenebrutinib (i.e., predictive biomarkers), are early surrogates of efficacy, are associated with progression to a more severe disease state (i.e., prognostic biomarkers), are associated with acquired resistance to fenebrutinib, are associated with susceptibility to developing adverse events or can lead to improved adverse event monitoring or investigation, can provide evidence of fenebrutinib activity (i.e., pharmacodynamic biomarkers), or can increase the knowledge and understanding of disease biology and drug safety. Biomarker endpoints may include, but are not limited to the following endpoints:

Relationship between baseline biomarkers in blood (serum and/or plasma and/or RNA) and efficacy, PK, or other biomarker endpoints Relationship between change from baseline to post-treatment sampling in blood biomarkers (serum and/or plasma and/or RNA) and efficacy, PK, or other biomarker endpoints Relationship between genetics, including, but not limited to, HLA genotype, efficacy, PK, or other biomarker endpoints Health Status Utility Objective The exploratory health status utility objective for this study is to evaluate health status utility scores of patients treated with fenebrutinib on the basis of the following endpoint:

Relationship between EuroQol 5-Dimension, 5-Level Questionnaire (EQ-5D-5L) index score and clinical measurements that may support pharmacoeconomic modeling Detailed Study Design This is a Phase III, randomized, multicenter, double-blind, double-dummy, parallel-group study to evaluate efficacy and safety of fenebrutinib in patients with RMS.

This study will consist of the following:

Screening

Double-blind treatment phase (DBT),

Double-blind safety follow-up (DBT-SFU),

Optional Open-label extension (OLE)

OLE safety follow-up (OLE-SFU) phase.

The screening phase will last approximately 4 weeks. Patients who fail screening will be allowed a maximum of one re-screening.

During the double-blind treatment phase, patients will be assessed in the clinic for efficacy and safety every 4 weeks for the first 24 weeks and then every 12 weeks thereafter. All eligible patients will be randomized 1:1 to daily oral fenebrutinib (200 mg twice daily [BID]) or daily oral teriflunomide (14 mg once daily [QD]) in the double-blind treatment phase.

The duration of the DBT phase is partially event-driven. The primary analysis will occur when approximately 180 cCDP12 events have occurred and when all patients have participated in the DBT phase for at least 96 weeks. The DBT phase is considered completed when the results of the primary analysis are disclosed and the study becomes unblinded to sites.

Patients who discontinue study treatment for any reason during the DBT phase will remain in the DBT phase but will not receive study treatment. These patients will continue to attend the DBT visits as scheduled but will have abbreviated efficacy and safety assessments.

At the end of the DBT phase, patients will enter an 8-week DBT-SFU if patients remained on study treatment at the end of the DBT phase and do not wish to participate in the OLE or if patients discontinued study drug less than 8 weeks from the end of the DBT.

At the end of the DBT phase, if the primary analysis and the benefit-risk assessment of the use of fenebrutinib therapy are positive, an optional OLE phase is planned for eligible patients who complete the DBT phase and who, in the opinion of the investigator, could benefit from fenebrutinib treatment. Patients may receive open-label fenebrutinib until fenebrutinib is commercially available in the patient's country; as per local regulations; or until the Sponsor decides to terminate the fenebrutinib RMS program. Treatment with open-label fenebrutinib will not exceed 4 years.

Patients who discontinue OLE fenebrutinib early or who complete the OLE phase will enter the OLE-SFU. Patients will be followed for safety for approximately 8 weeks.

Patient Population

Approximately 524 patients will be enrolled in this study.

Inclusion Criteria

Patients must meet the following criteria for study entry:

Signed Informed Consent Form

Age 18-65 years inclusive at time of signing Informed Consent Form

Ability to comply with the study protocol, in the investigator's judgment

EDSS score from 0 to 6.5 inclusive at screening

A diagnosis of RMS as defined by protocol criteria.

Neurologically stable for at least 30 days prior to randomization and baseline assessments Ability to complete the 9-HPT for each hand in <240 seconds Ability to perform T25FWT Patients currently receiving proton-pump inhibitors (PPIs) or H2-receptor agonists must be treated at a stable dose during the screening period prior to the initiation of study drug on Day 1 and to have a plan to remain at a stable dose for the duration of study treatment Patients must not initiate PPIs or H2Ras within 2 weeks of randomization.

Patients requiring symptomatic treatment of MS (e.g., fampridine, cannabis) and/or physiotherapy must be treated at a stable dose during the screening period prior to the initiation of study drug on Day 1 and must have a plan to remain at a stable dose for the duration of study treatment Patients must not initiate symptomatic treatment of MS or physiotherapy within 4 weeks of randomization For women of childbearing potential: agreement to remain abstinent (refrain from heterosexual intercourse) or use contraception with a failure rate of <1% per year during the treatment period, for 28 days after the final dose of study medication, and before the required accelerated elimination protocol is performed. Women must refrain from donating eggs during this same period. Hormonal contraceptive methods must be supplemented by a barrier method.

For men: agreement to remain abstinent (refrain from heterosexual intercourse) or use a condom, and agreement to refrain from donating sperm.

Exclusion Criteria

Patients who meet any of the following criteria will be excluded from study entry:

- A diagnosis of primary progressive MS or non-active secondary progressive MS
- Any known or suspected active infection at screening or baseline, or any major episode of infection requiring hospitalization or treatment with IV anti-microbials within 8 weeks prior to and during screening or treatment with oral anti-microbials within 2 weeks prior to and during screening
- History of confirmed or suspected progressive multifocal leukoencephalopathy (PML)
- History of cancer, including hematologic malignancy and solid tumors, within 10 years of screening. Basal or squamous cell carcinoma of the skin that has been excised and is considered cured and in situ carcinoma of the cervix treated with apparent success by curative therapy >1 year prior to screening is not exclusionary.
- Known presence of other neurologic disorders, including, but not limited to, the following:
  - History of ischemic cerebrovascular disorders (e.g., stroke, transient ischemic attack, spontaneous intracranial hemorrhage, or traumatic intracranial hemorrhage) or ischemia of the spinal cord
  - History or known presence of CNS or spinal cord tumor (e.g., meningioma, glioma)
  - History or known presence of potential metabolic causes of myelopathy (e.g., untreated vitamin B12 deficiency)
  - History or known presence of infectious causes of myelopathy (e.g., syphilis, Lyme disease, HTLV-1, herpes zoster myelopathy)
  - History of genetically inherited progressive CNS degenerative disorder (e.g., hereditary paraparesis, mitochondrial myopathy, encephalopathy, lactic acidosis, stroke [MELAS] syndrome)
  - Neuromyelitis optica spectrum disorder
  - History or known presence of systemic autoimmune disorders potentially causing progressive neurologic disease (e.g., lupus, anti-phospholipid antibody syndrome, Sjögren syndrome, Behçet disease)
  - History or known presence of sarcoidosis
  - History of severe, clinically significant brain or spinal cord trauma (e.g., cerebral contusion, spinal cord compression)
- Evidence of clinically significant cardiovascular (including arrhythmias or QTc prolongation), psychiatric, pulmonary, renal, hepatic, endocrine (including uncontrolled diabetes, non-gallstone pancreatitis, or chronic pancreatitis), metabolic, or gastrointestinal disease that, in the investigator's opinion, would preclude patient participation
- Patients meeting the New York Heart Association Class III and Class IV criteria for congestive heart failure
- Screening 12-lead ECG that demonstrates clinically relevant abnormalities that may affect patient safety or interpretation of study results including QT interval corrected through use of Fridericia's formula>440 ms demonstrated by at least two ECGs>30 minutes apart
- Current treatment with medications that are well known to prolong the QT interval at doses that have a clinically meaningful effect on QT, as determined by the investigator
- History of ventricular dysrhythmias or risk factors for ventricular dysrhythmias such as long QT syndrome and other genetic risk factors (e.g., Brugada syndrome); structural heart disease; coronary heart disease (symptomatic or with ischemia demonstrated by diagnostic testing, prior coronary artery bypass grafting, or coronary lesions>70% diameter stenosis that have not been or cannot be re-vascularized); clinically significant electrolyte abnormalities (e.g., hypokalemia, hypomagnesemia, hypocalcemia); family history of sudden, unexplained death; or cardiac ion channel genetic mutations (e.g., congenital long QT syndrome)
- Hypoproteinemia (e.g., in case of severe liver disease or nephrotic syndrome) with serum albumin<3.0 g/dL
- Moderate to severe impairment of renal function, as shown estimated glomerular filtration rate (eGFR)<60 mL/min/1.73 $m^2$ (may be repeated if eGFR 45-59 mL/min/1.73 $m^2$)
- Patients with significantly impaired bone marrow function or significant anemia, leukopenia, or thrombocytopenia and/or any of the following laboratory results:
  - Hemoglobin<9.5 g/dL (may be repeated if 9-9.4 g/dL)
  - Absolute white cell count<4000 cells/$mm^3$ (μL)
  - Platelet count<100 cells×$10^{9L}$ (may be repeated if 80-100×$10^9$/L)
  - Absolute neutrophil≤1500 cells/$mm^3$ (μL)
- Any concomitant disease that may require chronic treatment with systemic corticosteroids or immunosuppressants during the course of the study
- History of alcohol or other drug abuse within 12 months prior to screening
- Pregnant or breastfeeding, or intending to become pregnant during the study or 6 or 12 months (as applicable from the local label) after final dose of study drug
  - All women of childbearing potential will have a serum pregnancy test at screening. Urine pregnancy tests will be performed locally at specified subsequent visits. If a urine pregnancy test is positive, it must be confirmed by a serum pregnancy test (performed locally).
- Positive screening tests for active, latent, or inadequately treated hepatitis B (as evidenced by either of the following):
  - Positive hepatitis B surface antigen
  - Positive hepatitis B core antibody [total HBcAb] with detectable Hep B virus DNA
- Positive screening tests for hepatitis C (positive hepatitis C antibodies).
- Evidence of active or latent or inadequately treated infection with tuberculosis (TB) as defined by the following:
  - A positive QuantiFERON TB-Gold (QFT) test at screening or within the 3 months prior to screening. If QFT is unavailable, a negative Mantoux purified protein derivative skin test, as defined by the Centers for Disease Control and Prevention guidelines, may be performed at the screening visit or within the 3 months prior to screening and read locally.
  - Patients with a history of Bacille Calmette-Guerin vaccination should be screened using the QFT test only.
  - An indeterminate QFT test should be repeated.
  - A positive QFT test or two successive indeterminate QFT results should be considered positive diagnostic TB test.
  - An indeterminate QFT test followed by a negative QFT test should be considered a negative diagnostic TB test.
- Abnormalities in hepatic synthetic function tests (e.g., PT, INR, PTT, albumin) judged by the investigator to be clinically significant History of hospitalizations or transfusion for a gastrointestinal bleed Known bleeding diathesis Any condition possibly affecting oral drug absorption History of or currently active primary or secondary (non-drug-related) immunodeficiency, including known history of HIV infection or IgG<500 mg/dL Inability to complete an MRI scan (contraindications for MRI scan, including but not restricted to, pacemaker, cochlear implants, intracranial vascular clips, surgery within 6 weeks of entry in the study, coronary stent implanted within 8 weeks prior to the time of the intended MRI scan) or contraindication to gadolinium administration Any previous history of transplantation or anti-rejection therapy Adrenocorticotropic hormone or systemic corticosteroid therapy within 4 weeks prior to screening. The screening period may be extended for patients who have used systemic corticosteroids for MS before screening. For a patient to be eligible, systemic corticosteroids must not be administered between screening and baseline.

Treatment with IV Ig or plasmapheresis within 12 weeks prior to randomization

Sensitivity or intolerance to any ingredient (including excipients) of fenebrutinib or teriflunomide Receipt of a live-attenuated vaccine within 6 weeks prior to randomization. Influenza vaccination is permitted if the inactivated vaccine formulation is administered.

Need for systemic anti-coagulation (oral or injectable) or anti-platelet agent other than nonsteroidal anti-inflammatory drugs, aspirin, and other salicylates (aspirin up to 162 mg QD is allowed)

Previous treatment with fenebrutinib or another Bruton tyrosine kinase inhibitor for any indication Having one or more of the following laboratory results:

ALT or AST>2×upper limit of normal (ULN; may be repeated if 2-3×ULN)

Total bilirubin greater than 1.5×ULN (may be repeated if 1.6-3×ULN), with the exception for patients with Gilbert's disease

[a] Patients screened for this study should not be withdrawn from therapies for the sole purpose of meeting eligibility for the trial. Patients who discontinue their current therapy for non-medical reasons should specifically be informed of their treatment options before deciding to enter the study.

Example 2: A Phase III Multicenter, Randomized, Double-Blind, Double-Dummy, Parallel-Group Study to Evaluate the Efficacy and Safety of Fenebrutinib Compared with Teriflunomide in Adult Patients with Relapsing Multiple Sclerosis This Phase III study will evaluate the efficacy and safety of fenebrutinib compared with teriflunomide in adult patients with relapsing multiple sclerosis (RMS). The pharmacokinetics (PK) of fenebrutinib will also be evaluated. Specific objectives and corresponding endpoints for the study are outlined below Primary Efficacy Objective The primary efficacy objective for this study is to evaluate the efficacy of fenebrutinib compared with teriflunomide on the basis of the following co-primary endpoints:

Time to onset of composite 12-week confirmed disability progression (cCDP12), defined as the time from baseline to the first occurrence of a progression event according to at least one of the following three criteria; must be confirmed at a regularly scheduled visit that is at least 12 weeks after the initial disability progression:

An increase from baseline in Expanded Disability Status Scale (EDSS) score of ≥1.0 point in patients with a baseline EDSS score of ≤5.5 or an increase of ≥0.5 points in patients with a baseline EDSS score of >5.5 (confirmed disability progression [CDP])

≥20% increase from baseline in the Timed 25-Foot Walk Test (T25FWT)

≥20% increase from baseline in time to complete the 9-Hole Peg Test (9-HPT)

Annualized relapse rate (ARR)

Secondary Efficacy Objective

The secondary efficacy objective for this study is to evaluate the efficacy of fenebrutinib treatment compared with teriflunomide on the basis of the following endpoints:

Time to onset of composite 24-week confirmed disability progression (cCDP24)

Time to onset of CDP12, defined as an increase from baseline in EDSS score of ≥1.0 point in patients with a baseline EDSS score of ≤5.5 or an increase ≥0.5 points in patients with a baseline EDSS score of >5.5

Time to onset of 24-week CDP (CDP24)

Total number of gadolinium-enhancing lesions on T1-weighted MRI (T1Gd+) as detected by magnetic resonance imaging (MRI)

Total number of new and/or enlarging T2-weighted lesions as detected by MRI

Rate of percent change in total brain volume from Week 24 as assessed by MRI

Rate of change from baseline in patient-reported physical impacts of MS, as measured by the Multiple Sclerosis Impact Scale (29-Item), Version 2 (MSIS-29 v2) physical scale Time to onset of 12-week confirmed 4-point worsening in Symbol Digit Modalities Test (SDMT) score Change from baseline to Week 48 in the concentration of serum neurofilament light chain (NfL)

The secondary endpoints above do not reflect order of statistical hierarchy. The statistical hierarchy for the secondary endpoints is further discussed in the protocol, and details can be found in the Statistical Analysis Plan (SAP).

Exploratory Efficacy Objective

The exploratory efficacy objective for this study is to evaluate the efficacy of fenebrutinib compared with teriflunomide based on, but not limited to, the following endpoints:

Proportion of patients with worsening in SDMT by 4 points

Time to onset of ≥20% increase in 12-week confirmed T25FWT

Time to onset of ≥20% increase in 12-week confirmed 9-HPT

Time to onset of ≥20% increase in 24-week confirmed T25FWT

Time to onset of ≥20% increase in 24-week confirmed 9-HPT

Proportion of patients with a meaningful deterioration from baseline in patient-reported psychological impacts of MS, as assessed by the MSIS-29 v2 psychological scale at Week 96

Total number of new T1-hypointense lesions (black holes) from baseline as detected by MRI Proportion of patients who are free of protocol-defined relapse at Week 96 and at the time of clinical cutoff of the primary analysis Proportion of patients with a meaningful deterioration from baseline in patient-reported physical impacts of MS, as assessed by the MSIS-29 v2 physical scale, at Week 96

Proportion of patients free of disability progression, as assessed by cCDP12, cCDP24, CDP12, and CDP24, at Week 96 and at the time of clinical cutoff of primary analysis Note: In this study, the screening MRI measurements are used as the baseline measurements Safety Objective: The safety objective for this study is to evaluate the safety of fenebrutinib compared with teriflunomide on the basis of the following endpoints:

The nature, frequency, timing, and severity of adverse events; serious adverse events; and adverse events leading to study treatment discontinuation or dose interruptions Change from baseline in targeted vital signs Change from baseline in targeted ECG parameters Change from baseline in clinical laboratory results Proportion of patients with suicidal ideation or behavior, as assessed by the Columbia-Suicide Severity Rating Scale (C-SSRS)

Pharmacokinetic Objectives

The PK objective for this study is to characterize the fenebrutinib PK profile on the basis of the following endpoint:

Plasma concentration of fenebrutinib at specified time points

Sparse PK samples will be collected in all patients. However, to better characterize fenebrutinib PK in patients with MS, more intensive PK samples will be collected in a small subset of patients who consent for further evaluation.

The exploratory PK objectives for this study are as follows:

To evaluate potential relationships between drug exposure and the efficacy and safety of fenebrutinib on the basis of the following endpoints:

Relationship between plasma concentrations of fenebrutinib and efficacy endpoints Relationship between plasma concentrations of fenebrutinib and safety endpoints To evaluate potential relationships between selected covariates and exposure to fenebrutinib on the basis of the following endpoint:

Relationship between selected covariates and plasma concentrations of fenebrutinib Biomarker Objective The exploratory biomarker objective for this study is to identify and/or evaluate biomarkers that are predictive of response to fenebrutinib (i.e., predictive biomarkers), are early surrogates of efficacy, are associated with progression to a more severe disease state (i.e., prognostic biomarkers), are associated with acquired resistance to fenebrutinib, are associated with susceptibility to developing adverse events or can lead to improved adverse event monitoring or investigation, can provide evidence of fenebrutinib activity (i.e., pharmacodynamic [PD] biomarkers), or can increase the knowledge and understanding of disease biology and drug safety. Biomarker endpoints may include, but are not limited to, the following endpoints:

Relationship between baseline biomarkers in blood (serum and/or plasma, efficacy, PK, or other biomarker endpoints Relationship between change from baseline to post treatment sampling in blood biomarkers (serum and/or plasma) and efficacy, PK, or other biomarker endpoints Relationship between genetics, including, but not limited to, human leukocyte antigen (HLA) genotype, efficacy, PK, or other biomarker endpoints Exploratory biomarker analysis results may be reported separately from the clinical study report (CSR).

Health Status Utility Objective

The exploratory health status utility objective for this study is to evaluate health status utility scores of patients treated with fenebrutinib on the basis of the following endpoints:

Relationship between EuroQol 5 Dimension, 5 Level Questionnaire (EQ 5D 5L) index score and clinical measurements that may support pharmacoeconomic modeling Number of hospitalizations (e.g., collected since the last clinical visit)

Number of emergency room visits

Description of Study

This study is a Phase III, randomized, multicenter, double-blind, double-dummy, parallel-group study to evaluate the efficacy and safety of fenebrutinib compared with teriflunomide in adult patients with RRMS and active secondary progressive MS, collectively referred to as RMS. All eligible patients will be randomized 1:1 through an interactive voice or web-based response system (IxRS) to either one of two arms:

Fenebrutinib treatment arm: fenebrutinib (200 mg by mouth [PO] BID) with teriflunomide-matching placebo Teriflunomide treatment arm: teriflunomide (14 mg PO QD) with fenebrutinib-matching placebo in a blinded fashion Approximately 734 patients will be enrolled and will be recruited globally. Patients who discontinue study treatment early or who discontinue from the study for any reason will not be replaced. This study will consist of the following phases:

Screening phase

Double-blind treatment (DBT) phase

Post-DBT-safety follow-up (post-DBT-SFU) phase

Optional open-label extension (OLE) phase

OLE safety follow-up (OLE-SFU) phase

The study duration will vary for each patient as a result of the primary analysis being event driven. Randomization will be stratified according to the following criteria:

Global Region (United States vs. non-United States)

EDSS score (<4.0 vs. ≥4.0)

Presence or absence of T1Gad+ lesions at screening

Screening Phase

The screening phase should be a maximum of 4 weeks. Patients who fail the initial screening may qualify for one re-screening opportunity (for a total of two screenings per patient). During re-screening, some screening procedures may not need to be repeated.

Patients who are candidates for enrollment in the study will be evaluated by the investigator to ensure all eligibility criteria are met. All patients must sign the Informed Consent Form prior to any study-related procedures (including screening evaluations) and prior to any changes to their existing medication for the purposes of enrollment in the study.

Procedures at screening will include collection of medical history, physical examination, complete neurological examination, a review of contraception methods, EDSS score, 9-HPT, T25FWT, ECG, MRI scan, and blood and urine samples.

Double-Blind Treatment Phase

The duration of the DBT phase is partially event-driven. The primary data analysis will occur when approximately 212 cCDP12 events have occurred and each randomized patient has at least 96 weeks of DBT. The DBT phase is considered completed when the results of the primary analysis are disclosed and the study becomes unblinded to sites. If the projected number of cCDP events (212) has not been reached when the last patient completes Week 96 in the DBT phase because of slower than anticipated disability progression rates, the DBT phase will continue until the required number of cCDP12 events for the primary analysis have occurred, to maintain statistical power to detect a treatment difference. As a result, the DBT phase may extend beyond 96 weeks for the initial group of patients enrolled in the study.

Study assessments will be performed as described in the schedule of activities. All eligible patients will be randomized 1:1 to either fenebrutinib 200 mg PO BID with teriflunomide-matching placebo or to teriflunomide 14 mg PO QD with fenebrutinib-matching placebo in the DBT phase. Patients who discontinue study treatment for any reason during the DBT phase will remain in the DBT phase following an abbreviated schedule of activities but will not receive study treatment.

Study drugs and matching placebo will be dispensed every 4 weeks for the first 24 weeks and every 12 weeks thereafter.

Semi-structured telephone interviews will be conducted during the DBT phase every 6 weeks (±3 days) between study visits. Patients with clinically significant findings from a semi-structured telephone interview should be brought into the clinic for an unscheduled visit.

Unscheduled visits may be scheduled at any time required. Assessments performed at unscheduled visits are indicated in the DBT schedule of activities. Patients requiring additional transaminase testing to satisfy the applicable, local labeling requirements for teriflunomide, and/or as deemed necessary by the investigator, can be performed using an unscheduled visit.

Procedures Following Double-Blind Treatment Phase Study Treatment Discontinuation Patients who discontinue study treatment for any reason during the DBT phase will remain in the DBT phase but will not receive study treatment. These patients will continue to attend the DBT visits as scheduled but will have abbreviated efficacy and safety assessments.

Without specific elimination procedures, it can take up to 2 years to lower plasma teriflunomide concentrations to 0.02 mg/L. Therefore, all patients (i.e., patients in both treatment arms) who discontinue study treatment during the DBT phase will undergo the accelerated teriflunomide elimination procedure (ATEP).

Post-Double-Blind Treatment-Safety Follow-Up Phase

At the end of the DBT phase, patients will enter a post-DBT-SFU phase that will last at least 8 weeks if one of the following criteria are met:

The patient remains on study treatment at the end of the DBT phase and does not wish to participate in the OLE.

The patient discontinued DBT fenebrutinib with fewer than 8 weeks of follow-up in the DBT phase.

Patients randomized to the teriflunomide treatment arm in the DBT phase must complete the ATEP during the post-DBT-SFU phase, preferably early in the phase. Patients in the teriflunomide treatment arm who start or plan to start on commercial teriflunomide in the post DBT-SFU phase will not be required to undergo the ATEP. Patients in the fenebrutinib treatment arm are not permitted to start a new DMT within the post-DBT-SFU phase before a washout period of at least 8 weeks. Only safety assessments will be collected during the post-DBT-SFU phase.

Optional Open-Label Extension Phase

At the end of the DBT phase, if the primary analysis and the benefit-risk assessment of the use of fenebrutinib therapy are positive, there is an optional umbrella OLE phase for studies of fenebrutinib 200 mg BID in adult patients with MS that is planned for eligible patients who complete the DBT phase on study treatment and who, in the opinion of the investigator, could benefit from fenebrutinib treatment. Eligible patients will need to provide consent for participation in the OLE phase. Patients who consent to participate in the OLE phase will be required to meet the eligibility criteria for the OLE phase prior to dispensing of fenebrutinib.

In the OLE phase, the open-label fenebrutinib treatment duration for each patient will be approximately 96 weeks, and the long-term safety and efficacy of fenebrutinib treatment will be evaluated in patients with RMS. The Sponsor may decide to extend the duration of the OLE.

If eligible, a patient who has completed the DBT phase and who does not immediately enter the OLE phase once it starts may reconsider and enter the OLE phase up to 8 weeks after the OLE phase begins. Entry will be evaluated on a case-by-case basis in consultation with the Sponsor.

Eligible patients who were randomized to the teriflunomide treatment arm in the DBT phase must undergo the ATEP before starting open-label fenebrutinib and will require additional laboratory visits at OLE Weeks 4, 8, 16, and 20 for transaminase testing. Patients participating in the OLE who were randomized to the fenebrutinib treatment arm in the DBT phase will start the OLE schedule of activities as soon as possible. All patients will have clinic visits every 12 weeks.

During the OLE phase, all patients will self-administer two 100-mg fenebrutinib tablets PO BID, for a total of four fenebrutinib tablets a day. Patients who complete or withdraw from the OLE phase will enter the OLE-SFU phase. Semi-structured telephone interviews will be conducted in the OLE phase every 6 weeks (±3 days) between study visits. Patients who have participated in other global MS studies of fenebrutinib 200 mg BID in adult patients and completed the study on study drug may be eligible for participation in the OLE.

Open-Label Extension-Safety Follow-Up Phase

Patients in the OLE phase who discontinue fenebrutinib early or who complete the OLE phase will enter the OLE-SFU phase. Patients will be followed for safety for approximately 8 weeks. Only safety assessments will be collected during the OLE-SFU phase. Patients will not start a new DMT until completing the OLE-SFU phase. Only safety assessments will be collected during the OLE-SFU phase.

Unscheduled Visits

Additional unscheduled visits, for the assessment of potential MS relapse, disease progression, new neurological symptoms, suspected pregnancy, clinically significant increases in transaminases, or other safety events may occur at any time during the study. Patients with new neurological symptoms suggestive of MS relapse or MS worsening should have an EDSS, 9-HPT, and T25FWT performed by the examining investigator as soon as possible and within 7 days of the onset of the new neurological symptoms. Patients requiring additional transaminase testing to satisfy the applicable, local labeling requirements for teriflunomide, and/or as deemed necessary by the investigators, can be performed using an unscheduled visit.

Number of Patients

Approximately 734 patients with RMS will be enrolled and will be recruited globally.

Inclusion Criteria

Patients must meet the following criteria for study entry:

- Signed Informed Consent Form
- Age 18-55 years inclusive at time of signing the Informed Consent Form
- Ability to comply with the study protocol
- EDSS score of 0-5.5 at screening
- A diagnosis of RMS* in accordance with the revised 2017 McDonald Criteria (Thompson et al. 2018) and one of the following:
  - At least two documented clinical relapses within the last 2 years or one documented clinical relapse within 12 months of screening (but not within the 30 days prior to screening)
  - Documented evidence of the presence of at least one T1Gd+ lesion on MRI in the 12 months prior to randomization
    - *RMS may include aSPMS as defined by Lublin 2014.
- Neurologically stable for at least 30 days prior to randomization and baseline assessments
- Ability to complete the 9-HPT for each hand in <240 seconds
- Ability to perform the T25FWT
- For women of childbearing potential: agreement to remain abstinent (refrain from heterosexual intercourse) or use contraception, and agreement to refrain from donating eggs. Hormonal contraceptive methods must be supplemented by a barrier method.
- For men: agreement to remain abstinent (refrain from heterosexual intercourse) or use a condom, and agreement to refrain from donating sperm.

Exclusion Criteria

Patients who meet any of the following criteria will be excluded from study entry:

- Disease duration of >10 years from the onset of symptoms and an EDSS score at screening <2.0
- Pregnant or breastfeeding, or intending to become pregnant during the study or within 8 weeks (with ATEP) after the final dose of study drug
  - Women of childbearing potential must have a negative serum pregnancy test at screening and negative urine pregnancy tests at all subsequent visits. If a urine pregnancy test is positive, it must be confirmed by a serum pregnancy test, ideally from the central laboratory.
- Men intending to father a child during the study or within 8 weeks (with ATEP) after final dose of study drug
- A diagnosis of PPMS or non-active SPMS
- Any known or suspected active infection at screening or baseline, or any major episode of infection requiring hospitalization or treatment with IV anti-microbials within 8 weeks prior to and during screening or treatment with oral anti-microbials within 2 weeks prior to and during screening
- History of confirmed or suspected progressive multifocal leukoencephalopathy (PML)
- History of cancer, including hematologic malignancy and solid tumors, within 10 years of screening
  - Basal or squamous cell carcinoma of the skin that has been excised and is considered cured and in situ carcinoma of the cervix treated with apparent success by curative therapy >1 year prior to screening is not exclusionary.
- Known presence of other neurological disorders, including, but not limited to, the following:
  - History of ischemic cerebrovascular disorders (e.g., stroke, transient ischemic attack, spontaneous intracranial hemorrhage, or traumatic intracranial hemorrhage) or ischemia of the spinal cord
  - History or known presence of CNS or spinal cord tumor (e.g., meningioma, glioma)
  - History or known presence of potential metabolic causes of myelopathy (e.g., untreated vitamin B12 deficiency)
  - History or known presence of infectious causes of myelopathy (e.g., syphilis, Lyme disease, HTLV-1, herpes zoster myelopathy)
  - History of genetically inherited progressive CNS degenerative disorder (e.g., hereditary paraparesis, mitochondrial myopathy, encephalopathy, lactic acidosis, and stroke-like episodes [MELAS] syndrome)
  - Neuromyelitis optica spectrum disorder
  - History or known presence of systemic autoimmune disorders potentially causing progressive neurological disease (e.g., lupus, anti-phospholipid antibody syndrome, Sjögren syndrome, Behçet disease)
  - History or known presence of sarcoidosis
  - History of severe, clinically significant brain or spinal cord trauma (e.g., cerebral contusion, spinal cord compression)
- Evidence of clinically significant psychiatric, pulmonary, renal, hepatic (including Gilbert syndrome), metabolic, gastrointestinal (GI), or cardiovascular disease (including arrhythmias or QTc prolongation), or endocrine disease (including uncontrolled diabetes, non-gallstone pancreatitis, or chronic pancreatitis) that, in the investigator's opinion, would preclude patient participation
- Presence of the New York Heart Association Class III and Class IV criteria for congestive heart failure
- Screening 12-lead ECG that demonstrates clinically relevant abnormalities that may affect patient safety or interpretation of study results, including QT interval corrected through use of Fridericia's formula (QTcF) >440 ms demonstrated by at least two ECGs>30 minutes apart
- Current treatment with medications that are well known to prolong the QT interval at doses that have a clinically meaningful effect on QT, as determined by the investigator
- History of ventricular dysrhythmias or risk factors for ventricular dysrhythmias, such as long QT syndrome and other genetic risk factors (e.g., Brugada syndrome); structural heart disease; coronary heart disease (symptomatic or with ischemia demonstrated by diagnostic testing, prior coronary artery bypass grafting, or coronary lesions>70% diameter stenosis that have not been or cannot be re-vascularized); clinically significant electrolyte abnormalities (e.g., hypokalemia, hypomagnesemia, hypocalcemia); family history of sudden, unexplained death; or cardiac ion channel genetic mutations (e.g., congenital long QT syndrome)
- Rare hereditary problems of galactose intolerance, total lactase deficiency, or glucose-galactose malabsorption
- Hypoproteinemia (e.g., in case of severe liver disease or nephrotic syndrome) with serum albumin<3.0 g/dL
- Patients with severe renal impairment undergoing dialysis and/or estimated glomerular filtration rate (eGFR)<60 mL/min/1.73 $m^2$ (may be repeated if eGFR 45-59 mL/min/1.73 $m^2$)
- Severe hepatic disease impairment (Child-Pugh Class C)

One or more of the following laboratory results:
- ALT or AST>2×upper limit of normal (ULN; may be repeated if 2-3×ULN)
- Total bilirubin greater than 1.5×ULN (may be repeated if 1.6-3×ULN), with the exception of patients with Gilbert syndrome
- Persisting elevations of serum amylase or lipase greater than 2×ULN Patients with significantly impaired bone marrow function or significant anemia, leukopenia, neutropenia or thrombocytopenia, and/or any of the following laboratory results:
- Hemoglobin<9.5 g/dL (may be repeated if 9-9.4 g/dL)
- Absolute white cell count<4000 cells/mm$^3$ (μL)
- Platelet count<100 cells×10$^9$/L (may be repeated if 80-100×10$^9$/L)
- Absolute neutrophil≤1500 cells/mm$^3$ (μL)

Any concomitant disease that may require chronic treatment with systemic corticosteroids or immunosuppressants during the course of the study History of alcohol or other drug abuse within 12 months prior to screening Positive screening tests for active, latent, or inadequately treated hepatitis B (as evidenced by either of the following):
- Positive hepatitis B surface antigen (HBsAg)
- Positive hepatitis B core antibody [total HBcAb] with detectable hepatitis B virus (HPV) DNA Positive screening tests for hepatitis C (positive hepatitis C antibodies)

Evidence of active or latent or inadequately treated infection with tuberculosis (TB) as defined by the following:
- A positive QuantiFERON TB-Gold (QFT) test found at screening. QFT testing must be performed through the central laboratory.
- Patients with a history of Bacille Calmette-Guérin vaccination should be screened using the QFT test only.
- An indeterminate QFT test should be repeated.
- A positive QFT test or two successive indeterminate QFT results should be considered positive diagnostic TB test.
- An indeterminate QFT test followed by a negative QFT test should be considered a negative diagnostic TB test.

Abnormalities in hepatic synthetic function tests (e.g., PT, INR, aPTT) judged by the investigator to be clinically significant History of hospitalization or transfusion for a GI bleed Known bleeding diathesis Any condition possibly affecting oral drug absorption History of or currently active primary or secondary (non-drug-related) immunodeficiency, including known history of HIV infection Patients with IgG<500 mg/dL Inability to complete an MRI scan (contraindications for MRI scan, including but not restricted to, pacemaker, cochlear implants, intracranial vascular clips, surgery within 6 weeks of entry in the study, coronary stent implanted within 8 weeks prior to the time of the intended MRI scan) or contraindication to gadolinium (Gd) administration Any previous history of transplantation or anti-rejection therapy Adrenocorticotropic hormone or systemic corticosteroid therapy within 4 weeks prior to screening.
- For a patient to be eligible, systemic corticosteroids must not be administered between screening and baseline.

Receiving an unstable dosing regimen of proton pump inhibitors (PPIs) or $H_2$-receptor agonists ($H_2$RAs) during the screening phase prior to the initiation of study drug and/or no plan to remain at a stable dose for the duration of study treatment
- Patients must not initiate PPIs or H2RAs within 2 weeks of randomization.

Receiving an unstable regimen of symptomatic treatment of MS (e.g., fampridine, cannabis). Patients must be treated at a stable dose during the screening phase prior to the initiation of study drug and and/or no plan to remain at a stable dose for the duration of study treatment
- Patients must not initiate symptomatic treatment of MS within 4 weeks of randomization.
- Patients must not initiate physiotherapy within 4 weeks of randomization.

Treatment with IV Ig or plasmapheresis within 12 weeks prior to randomization

Sensitivity or intolerance to any ingredient (including excipients) of fenebrutinib or teriflunomide Previously discontinued teriflunomide therapy for safety and/or efficacy reasons Receipt of a live-attenuated vaccine within 6 weeks prior to randomization
- Influenza vaccination is permitted if the inactivated vaccine formulation is administered.

Need for systemic anticoagulation (oral or injectable) or anti-platelet agent other than nonsteroidal anti-inflammatory drugs, aspirin, and other salicylates (aspirin up to 162 mg QD is allowed)

Previous treatment with fenebrutinib or another BTK inhibitor for any indication Patients with a history of a hypersensitivity reaction to teriflunomide, leflunomide, or to any inactive ingredients in teriflunomide Treatment with strong CYP3A4 inhibitors, strong or moderate CYP3A4 inducers, within 7 days or 5 drug-elimination half-lives (whichever is longer) prior to randomization Treatment with CYP3A4 substrates with a narrow therapeutic window within 7 days or 5 drug-elimination half-lives (whichever is longer) prior to randomization Previous use of anti-CD20 therapies, including ocrelizumab, unless the last infusion was more than 2 years prior to screening, B-cell count is normal at screening, and treatment discontinuation was not motivated by safety reasons or lack of efficacy[a]

Previous use of fingolimod, siponimod, or ozanimod within 8 weeks of randomization[a]

Previous use of natalizumab for more than 1 year and within 6 months of randomization[a]

Previous treatment with mycophenolate mofetil or methotrexate within 12 weeks of randomization[a]

Previous use of teriflunomide within the last 24 months, unless teriflunomide plasma concentrations are <0.02 mg/L at screening[a]

Any previous treatment with cladribine, mitoxantrone, daclizumab, alemtuzumab, or cyclophosphamide Treatment with any investigational agent (including high-dose biotin) within 24 weeks prior to screening or 5 half-lives of the investigational drug (whichever is longer), or treatment with any experimental procedure for MS (e.g., treatment for chronic cerebrospinal venous insufficiency)

Requirement for any prohibited concomitant medications

Chronic use of cholestyramine or activated charcoal

Previous treatment with any other immunomodulatory or immunosuppressive medication not already listed above without appropriate washout as described in the applicable local label If the washout requirements are not described in the applicable local label, then the wash out period must be 5 times the half-life of the medication. The PD effects of the previous medication must also be considered when determining the required time for washout. [a]

[a] Patients screened for this study should not be withdrawn from therapies for the sole purpose of meeting eligibility for the trial. Patients who discontinue their current therapy for non-medical reasons should specifically be informed of their treatment options before deciding to enter the study.

Eligibility Criteria for Open-Label Extension Phase

Patients who meet the following criteria may participate in the OLE phase:

Completed the DBT phase of the study (remaining on study treatment; no other DMT administered) and who, in the opinion of the investigator, may benefit from treatment with fenebrutinib Able and willing to provide signed Informed Consent Form to participate in the OLE phase and to comply with the study protocol Patients randomized to the teriflunomide treatment arm during the DBT phase must undergo the ATEP prior to the first administration of open-label fenebrutinib For women of childbearing potential: agreement to remain abstinent (refrain from heterosexual intercourse) or use contraception, and agree to refrain from donating eggs. Hormonal contraceptive methods must be supplemented by a barrier method.

For men: agreement to remain abstinent (refrain from heterosexual intercourse) or use a condom, and agreement to refrain from donating sperm.

Length of Study

The duration of the DBT phase will be approximately 188 weeks or approximately 3.5 years (assuming last patient randomized after 92 weeks+96 weeks of DBT for the last patient into the study). The maximum length of the study, from screening of the first patient to the end of the study, is expected to be approximately 292 weeks or approximately 5.5 years (assuming 92 weeks of recruitment+96 weeks of DBT+96 weeks in OLE+8 weeks of OLE SFU for the last patient into study).

Fenebrutinib and Fenebrutinib-Matching Placebo

Patients will take two 100 mg tablets PO BID for a total dose of 400 mg of fenebrutinib (or placebo) every day. Patients will self-administer two 100 mg tablets in the morning and two 100 mg tablets in the evening by mouth. Fenebrutinib (or matching placebo) may be taken orally with or without food. The tablet should be swallowed whole with some water, can be taken with or without food, and should be taken at the same time each day. Patients should be instructed that a missed fenebrutinib (or matching placebo) dose should not be taken with the next scheduled dose. Administration of fenebrutinib (or matching placebo) should be staggered with antacid use (i.e., study drug should be taken 2 hours before or 2 hours after antacid administration). In addition, any antacids (e.g., bismuth subsalicylate, calcium carbonate, aluminum-magnesium hydroxide) should be recorded as concomitant medications.

Teriflunomide and Teriflunomide-Matching Placebo

The comparator, teriflunomide (or matching placebo), will be administered as one 14 mg capsule PO QD (1 capsule per day) every day. The capsule should be swallowed whole with some water, can be taken with or without food, and should be taken at the same time each day. Patients should be instructed that a missed dose should not be taken with the next scheduled dose.

Statistical Methods

Primary Analysis

There are two co-primary analyses to compare between the fenebrutinib group and the teriflunomide group: time from randomization to cCDP12 and annualized rate of protocol-defined relapses from randomization to time of primary analysis. If at least one of the two co-primary analyses are statistically significant, then the trial is considered positive. Type I error will be controlled using a fallback procedure (reference Food and Drug Administration [FDA] guidance on Multiple Endpoints in Clinical Trials].

Time to onset of composite 12-week cCDP12, defined as the time from baseline to the first occurrence of a progression event according to at least one of the following three criteria must be confirmed at a regularly scheduled visit that is at least 12 weeks after the initial disability progression:

An increase from baseline in EDSS score of ≥1.0 point in patients with a baseline EDSS score of ≤5.5 or ≥0.5 points in patients with a baseline EDSS score of >5.5 (confirmed disability progression [CDP])

≥20% increase from baseline in T25FWT

≥20% increase from baseline in time to complete the 9-HPT

The specific composite component that generated the initial composite disability progression event is required for confirmation of cCDP. All assessments between initial event and the confirmation visit need to satisfy the definition of a composite disability progression event to be confirmed. Assessments occurring within 90 days after a protocol-defined relapse will not be used for confirmation of initial disease progression. Patients who prematurely discontinue study treatment will be asked to continue with the study-specified assessments, and every effort will be made to follow up on their primary and secondary assessments at the next scheduled visit. All initial disability progression events with corresponding confirmation visits at the next scheduled visit will be considered for the statistical analysis regardless of whether the patient discontinued study treatment or the confirmation visit occurred during the DBT phase.

ARR:

Protocol-defined relapse is defined as the occurrence of new or worsening neurological symptoms attributable to MS. Symptoms must persist for >24 hours and should not be attributable to confounding clinical factors (e.g., fever, infection, injury, adverse reactions to medications) and immediately preceded by stable or improving neurological state for at least 30 days. The new or worsening neurological symptoms must be accompanied by objective neurological worsening consistent with an increase of at least half a step on the EDSS scale, or 2 points on one of the appropriate FSS, or 1 point on 2 or more of the appropriate FSS. The change must affect the selected FSS (i.e., pyramidal, ambulation, cerebellar, brainstem, sensory or visual). Episodic spasms, sexual dysfunction, fatigue, mood change or bladder or bowel urgency or incontinence will not suffice to establish a relapse.

Derivation of protocol-defined relapses will be performed by the Sponsor based on pre-specified criteria. The derivation will be applied to data collected on the clinical relapse event by the treating investigator, and the corresponding EDSS and FSS scores provided by the examining investigator.

Determination of Sample Size

The purpose of this study is estimation and hypothesis testing regarding the effect of fenebrutinib on co-primary endpoints of time from baseline to cCDP12 and ARR by the time of primary analysis. P-value and point and interval estimates will be obtained for a) the true underlying hazard ratio for time from baseline to cCDP12 and b) the true underlying annualized relapse rate ratio.

The sample size of this trial is based on testing the null hypothesis of no difference between the control and experimental arms. This study will enroll approximately 734 patients with an expected recruitment of 92 weeks. The primary analysis is based on approximately 212 cCDP12 events for the time to cCDP12 endpoint, and all protocol-defined relapse events happened from randomization to the time of primary analysis for the ARR endpoint. This sample size is driven by the primary efficacy and a series of statistical assumptions.

Prohibited Therapies

Medications in the following categories should be prohibited for 7 days or 5 half-lives, whichever is longer, prior to the first dose of study drug until the final dose of study drug:

Strong CYP3A4 inhibitors

Strong or moderate CYP3A inducers

The following medications should be prohibited during study treatment:

CYP3A4 substrates with a narrow therapeutic window

Table 1 summarizes a list of prohibited medications. This list is not comprehensive:

| Class | Examples of Drugs in this Class |
|---|---|
| Strong CYP3A4 inhibitors | Boceprevir, cobicistat, clarithromycin, danoprevir/ritonavir, elvitegravir/ritonavir, indinavir/ritonavir, itraconazole, idelalisib, ketoconazole, lopinavir/ritonavir, nefazodone, nelfinavir, posaconazole, ritonavir, saquinavir, telaprevir, telithromycin, and voriconazole |
| Strong CYP3A inducers | Apalutamide, carbamazepine, enzalutamide, mitotane, phenytoin, rifampin, and hyperforin (St. John's Wort) |
| Moderate CYP3A inducers | Bosentan, dexamethasone, efavirenz, etravirine, phenobarbital, primidone, phenobarbital, and rifabutin |
| CYP3A4 substrate with a narrow therapeutic window | Alfentanil, astemizole, cyclosporine, cisapride, dihydroergotamine, ergotamine, everolimus, fentanyl, pimozide, quinidine, sirolimus, terfenadine, and tacrolimus |

Other Prohibited Therapies

Use of the following concomitant therapies is prohibited as described below for patients in the DBT phase who remain on study treatment, in the OLE phase, and in the OLE-SFU phase:

- Investigational therapy (other than protocol-mandated study treatment)
- Any B-cell targeted therapy (e.g., rituximab, alemtuzumab, atacicept, belimumab, ofatumumab, or ocrelizumab)
- BTK inhibitors (other than fenebrutinib)
- Any other DMT for MS (including, but not limited to, high-dose biotin, cladribine, mitoxantrone, interferons, dimethyl fumarate and other fumarates, and fingolimod and other sphingosine-1-phosphate receptor modulators)
- Systemic anti-coagulation (oral or injectable) or anti-platelet agent other than nonsteroidal anti-inflammatory drugs, aspirin, and other salicylates (aspirin up to 162 mg once daily is allowed)
- Use of stand-alone doses of acid-reducing agents (e.g., PPIs, H2RAs) at visits requiring PK sampling is prohibited.

Use of the following concomitant therapy is prohibited as described below during the DBT phase for patients who discontinue DBT treatment and the DBT-SFU:

- Investigational therapy (other than protocol-mandated study treatment)

Caution is advised when administering a DMT after fenebrutinib use. There are insufficient data available regarding the risk associated with switching from fenebrutinib to other products.

Table 2 summarizes a list of medications that may be administered concomitantly but such administration may include certain cautions. This list is not comprehensive:

| Class | Recommendation | Examples of Drugs in this Class |
|---|---|---|
| Antacids | Take fenebrutinib 2 hours before or 2 hours after antacid | Bismuth subsalicylate, calcium carbonate, aluminum-magnesium hydroxide (e.g., Maalox ®, Pepto-Bismol ®, Rolaids ®) |
| Breast cancer resistance protein (BCRP) substrates | Use with caution and monitor for adverse events related to BCRP substrates as directed by product labeling | Anti-hypertensive (prazosin)<br>Anti-inflammatory (sulfasalazine)<br>Lipid-lowering (rosuvastatin [recommended maximum dose: 10 mg/day], atorvastatin [recommended maximum dose: 20 mg/day])<br>Muscle relaxants (dantrolene)<br>Steroids (estrone-3-sulfate) |
| Sensitive CYP3A substrates | Use with caution and monitor for adverse events related to CYP3A substrates as directed by product labeling | Antiemetic/prokinetic (aprepitant)<br>Anti-histamine (astemizole)<br>Anti-hypertensive/cardiac (dronedarone, eplerenone, felodipine, nisoldipine, ticagrelor, vardenafil)<br>Benzodiazepines (alprazolam, diazepam, midazolam)<br>Lipid-lowering (simvastatin [recommended maximum dose: 10 mg/day], lovastatin |

-continued

| Class | Recommendation | Examples of Drugs in this Class |
|---|---|---|
| | | [recommended maximum dose: 20 mg/day])<br>Migraine (eletriptan, ergotamine)<br>Steroids (budesonide, fluticasone)<br>Other (buspirone, conivaptan, darifenacin, dasatinib, lurasidone, quetiapine, sildenafil, tolvaptan, triazolam) |

Example 3: A Phase III Multicenter, Randomized, Double-Blind, Double-Dummy, Parallel-Group Study to Evaluate the Efficacy and Safety of Fenebrutinib Compared with Teriflunomide in Adult Patients with Relapsing Multiple Sclerosis This Phase III study will examine the efficacy and safety of fenebrutinib compared with teriflunomide in adult subjects with RMS. The specific objectives, corresponding endpoints, inclusion criteria, exclusion criteria, and other aspects of this study are as described in Example 2 above, but wherein Annulazed Relapse Rate (ARR) is the sole primary endpoint, and time to onset of composite 12-week confirmed disability progression (cCDP12) is a secondary end point.

Example 4: Comparison of In Vitro Properties of BTK Inhibitors

The in vitro properties of the three BTK inhibitors fenebrutinib, evobrutinib, and tolebrutinib are compiled in Table 3. Evobrutinib and tolebrutinib are covalent inhibitors, whereas fenebrutinib is a non-covalent inhibitor. The kinase selectivities of fenebrutinib, evobrutinib, tolebrutinib, and the covalent BTK inhibitor ibrutinib are also shown in FIG. 1.

BTK inhibitory potency ($IC_{50}$) and kinase selectivity of fenebrutinib (FEN), evobrutinib (EVO), and tolebrutinib (TOL) were assessed internally or in a commercial panel of over 200 human kinases. FEN, TOL, and EVO were screened at 1 μM, and EVO was also screened at 10 μM because it has a weaker BTK $IC_{50}$ than FEN and TOL. $IC_{50}$ values were determined for all kinases inhibited by at least 50% in the initial screen at 1 or 10 μM. To demonstrate that the selectivity values determined using the $IC_{50}$ values are relevant for the covalent inhibitors EVO and TOL, their covalent reactivity, or $k_{inact}/K_i$ inactivation efficiency, was measured in biochemical assays by monitoring in real time the competition by the covalent inhibitors with a fluorescent active site ligand against BTK and BMX. FEN was also tested in human whole blood for its ability to block activation of B cells (CD69) and basophils (CD63). The rate of FEN release from the BTK•FEN complex was quantified in a biochemical preincubation-dilution experiment, where BTK activity was recovered with a rate constant $k_{off}$ and residence time $1/k_{off}$.

FEN potently inhibits BTK ($IC_{50}$=2.3 nM); TOL inhibits BTK with $IC_{50}$=1.5 nM, whereas EVO is much less potent ($IC_{50}$=32 nM). In whole blood, FEN potently blocks activation of B cells (CD69 $IC_{50}$=8 nM) and basophils (CD63 $IC_{50}$=31 nM). In the kinase panel, FEN (1 μM) inhibits by >50% only 3/286 off-target kinases, whereas TOL (1 μM) inhibits 19/218 off-target kinases. EVO inhibits 3/221 off-target kinases at 1 μM, but at 10 μM it inhibits 18/218 kinases. Based on kinase $IC_{50}$ values, FEN is >130-fold selective against all 286 kinases tested, whereas EVO is <75-fold selective vs. Bmx (0.5×), TEC (2×), ErbB4 (10×), Blk (23×), and Flt3 (71×). TOL is <10-fold selective vs. BMX, BLK, ERBB4, TXK and LCK, and inhibits eleven additional kinases with <100-fold selectivity (Src, Fgr, TEC, RIPK2, BRK, CSK, YES, ERBB2, EGFR, HCK, and SRM). The difference in kinase selectivity among the tested compounds is further illustrated in FIG. 1. In addition, the covalent kinetic selectivity of EVO and TOL, as assessed by the ratio of $k_{inact}/K_i$ for BMX vs. BTK (EVO=0.5, TOL=1), was found to be nearly equal to the $IC_{50}$ selectivity for these inhibitors against these kinases (EVO=0.5, TOL=2). Finally, in a preincubation-dilution assay, the BTK•FEN complex demonstrated high stability; FEN dissociates slowly from BTK and shows a residence time of 18.3 hours bound to BTK. The slow dissociation kinetics of fenebrutinib may positively influence efficacy. The high selectivity of fenebrutinib may result in a more favorable safety profile in RMS compared to less selective inhibitors, by limiting off-target effects. The non-covalent binding mechanism of fenebrutinib may also results in a more favorable safety profile in RMS than covalent inhibitors.

Table 3 summarizes in vitro properties of fenebrutinib, evobrutinib, and tolebrutinib

| | Parameter | Fenebrutinib | Evobrutinib | Tolebrutinib |
|---|---|---|---|---|
| Kinase Selectivity | # off-target kinases >50% INH/# total kinases tested @ 1 μM | 2/286 [a] | 3/221 [a] | 19/218 [d] |
| | BTK $IC_{50}$, nM (fold selectivity) | 2.3 (1) [a] | 31.7 (1) [a] | 1.5 (1) [d] |
| | Src $IC_{50}$, nM (fold selectivity) | 302 (131) [a] | — | 54 (36) [d] |
| | BMX $IC_{50}$, nM (fold selectivity) | 351 (153) [a] | 15 (0.5) [d] | 2.5 (2) [d] |
| | Fgr $IC_{50}$, nM (fold selectivity) | 387 (168) [a] | 2,330 (74) [d] | 33 (22) [d] |
| | BLK $IC_{50}$, nM (fold selectivity) | — | 727 (23) [d] | 3.0 (2) [d] |
| | ERBB4 $IC_{50}$, nM (fold selectivity) | — | 326 (10) [d] | 6.1 (4) [d] |
| | FLT3 $IC_{50}$, nM (fold selectivity) | — | 2,250 (71) [d] | — |
| | TEC $IC_{50}$, nM (fold selectivity) | — | 64.1 (2) [d] | 18 (12) [d] |
| | TXK $IC_{50}$, nM (fold selectivity) | — | 254 (8) [d] | 3.9 (3) [d] |
| | CK1e1 $IC_{50}$, nM (fold selectivity) | — | 1,450 (46) [d] | — |
| | CDK8/cycC $IC_{50}$, nM (fold selectivity) | — | 3,500 (110) [d] | — |
| | LCK $IC_{50}$, nM (fold selectivity) | — | 3,800 (120) [d] | 7.5 (5) [d] |

-continued

| | Parameter | Fenebrutinib | Evobrutinib | Tolebrutinib |
|---|---|---|---|---|
| | MLK2 $IC_{50}$, nM (fold selectivity) | — | 3,980 (126) [d] | — |
| | MKNK2 $IC_{50}$, nM (fold selectivity) | — | 4,130 (130) [d] | — |
| | FGFR1 $IC_{50}$, nM (fold selectivity) | — | 4,150 (131) [d] | — |
| | RIPK2 $IC_{50}$, nM (fold selectivity) | — | 4,330 (137) [d] | 125 (83) [d] |
| | ITK $IC_{50}$, nM (fold selectivity) | — | 4,640 (146) [d] | — |
| | BRK $IC_{50}$, nM (fold selectivity) | — | 6,020 (190) [d] | 44 (29) [d] |
| | CSK $IC_{50}$, nM (fold selectivity) | — | 7,820 (247) [d] | 87 (58) [d] |
| | RET $IC_{50}$, nM (fold selectivity) | — | 8,630 (272) [d] | — |
| | YES $IC_{50}$, nM (fold selectivity) | — | — | 16 (11) [d] |
| | ERBB2 $IC_{50}$, nM (fold selectivity) | — | — | 25 (17) [d] |
| | EGFR $IC_{50}$, nM (fold selectivity) | — | — | 60 (40) [d] |
| | HCK $IC_{50}$, nM (fold selectivity) | — | — | 91 (61) [d] |
| | SRM $IC_{50}$, nM (fold selectivity) | — | — | 116 (77) [d] |
| | LYN $IC_{50}$, nM (fold selectivity) | — | — | 194 (129) [d] |
| | FRK $IC_{50}$, nM (fold selectivity) | — | — | 231 (154) [d] |
| | TNK2 $IC_{50}$, nM (fold selectivity) | — | — | 847 (565) [d] |
| Covalent Reaction | BTK Ki, nM | NA | 290 [d] | 8.7 [d] |
| | BTK $k_{inact}$, $s^{-1}$ | NA | 0.0052 [d] | 0.00063 [d] |
| | BTK $k_{inact}/K_i$, $M^{-1}$ $s^{-1}$ | NA | 18,000 [d] | 58,100 [d] |
| Covalent Reaction | BMX Ki, nM | NA | 84 [d] | 42 [d] |
| | BTK $k_{inact}$, $s^{-1}$ | NA | 0.0032 [d] | 0.0029 [d] |
| | BTK $k_{inact}/K_i$, $M^{-1}$ $s^{-1}$ | NA | 38,100 [d] | 60,800 [d] |
| Covalent Kinetic Selectivity | (BTK $K_{inact}/K_i$)/(BMX $K_{inact}/K_i$) | NA | 0.5 [d] | 1.0 [d] |
| Kinetics and Residence Time | BTK residence time, h (jump dilution vs. 50 μM ATP) | 18.3 [a] | NA | NA |
| | BTK $K_i$, nM | 7.1 [d] | NA | NA |
| | BTK $K_i$*, nM | 0.17 [d] | NA | NA |
| | BTK residence time, h (competitive binding) | 6.6 [d] | NA | NA |
| Whole Blood | CD69 Whole Human Blood $IC_{50}$, nM | 8.4 [a] | 84 [b] | 10 [c] |
| | CD63 Whole Human Blood $IC_{50}$, nM | 30.7 [a] | 1,660 [b] | 166 [c] |

[a] Crawford, et al., *J Med Chem* 2018, 61: 2227-2245
[b] Haselmeyer, J Immunol 2019, 202: 2888-2906
[c] Francesco, ECTRIMS 2017 poster (PRN), available at <https://onlinelibrary.ectrims-congress.eu/ectrims/2017/ACTRIMS-ECTRIMS2017/200644/mrchelle.r.francesco.prn2246.a.potent.and.selective.blood.brain.barrier.html>
[d] unpublished
NA = not applicable Unpublished kinase selectivity data were obtained generally following the procedures of Crawford, et al., *J Med Chem* 2018, 61: 2227-2245 (SI pp S31-S32). Unpublished covalent reaction ($k_{inact}/K_i$) data were obtained generally following the procedures of Schnute, et al., *ACS Med Chem Lett* 2018, 10: 80-85 (SI pp S29-S31), using N-terminal His-tagged full-length recombinant human BTK. BTK residence time data were obtained following the procedures of Crawford, et al., *J Med Chem* 2018, 61: 2227-2245 (SI pp S43). Unpublished competitive binding kinetics data were obtained generally following the procedures of Schnute, et al., *ACS Med Chem Lett* 2018, 10: 80-85 (SI pp S29-S31), using N-terminal His-tagged full-length recombinant human BTK. The impact of ibrutinib, another covalent BTK inhibitor, on activation of B cells and basophils in human whole blood was also assessed (CD63 $IC_{50}$ nM=171; CD69 $IC_{50}$ nM=12; Crawford, et al., *J Med Chem* 2018, 61: 2227-2245).

Figure 2:
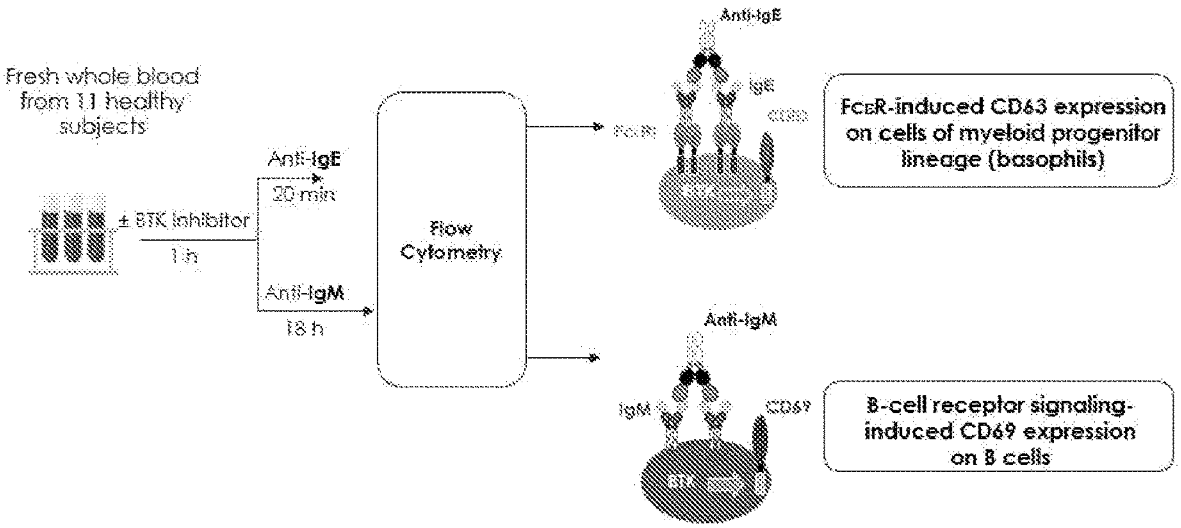
FIG. 2 provides a schematic to evaluate the effect of BTK inhibitors on B cell and myeloid progenitor lineage cell activation.

FIG. 2 is a schematic for in vitro B cell and myeloid progenitor lineage cell activation assays used to evaluate fenebrutinib, evobrutinib, and tolebrutinib. The EC50 values from these assays are provided in Tables 4 and 5 below. Head-to-head, fenebrutinib was the most potent BTKi when compared to evobrutinib and tolebrutinib in inhibition of $F_cR$ signaling in cells of myeloid progenitor lineage (basophils; Table 4), and in inhibition of B-cell receptor signalling in B cells (Table 5).

TABLE 4

Inhibition of myeloid lineage progenitor cell activation

| | Fenebrutinib | Evobrutinib | Tolebrutinib |
|---|---|---|---|
| $EC_{50}$, nM (±SEM) | 15 (4) | 171 (133) | 80 (11) |
| $EC_{90}$, nM (±SEM) | 62 (12) | 3102 (560) | 281 (49) |

TABLE 5

Inhibition of B cell activation

| | Fenebrutinib | Evobrutinib | Tolebrutinib |
|---|---|---|---|
| $EC_{50}$, nM (±SEM) | 8 (4) | 161 (42) | 26 (5) |
| $EC_{90}$, nM (±SEM) | 65 (28) | 524 (101) | 84 (25) |

Example 5: Summary of Safety of Fenebrutinib in a Large Population of Patients with Diverse Autoimmune Conditions, Other than Multiple Sclerosis Fenebrutinib has previously been evaluated in clinical trials for the autoimmune conditions rheumatoid arthritis (RA; Chan P, et al. Pharm Res. 2020, 37:25; Cohen S, et al. *Arthritis Rheumatol.* 2020. doi: 10.1002/art.41275; ClinicalTrials.gov: NCT02983227), systemic lupus erythematosus (SLE; ClinicalTrials.gov: NCT02908100; ClinicalTrials.gov: NCT03407482), and chronic spontaneous urticaria (CSU; ClinicalTrials.gov: NCT03693625; ClinicalTrials.gov: NCT03137069). The safety data from 792 patients in this studies taking 200 mg fenebrutinib twice daily, or placebo, was analyzed. A summary of the adverse events observed is provided in Table 6. Adverse events were mostly non-serious in patients with autoimmune conditions treated with fenebrutinib. Asymptomatic and reversible liver aminotransferase elevations were the only risk causally associated with fenebrutinib. There were no other signs of hepatic dysfunction, no Hy's law cases, and elevations returned to baseline/normal with treatment cessation.

TABLE 6

Summary of adverse events (AE) observed in previous clinical trials at highest fenebrutinib dose.

| | Fenebrutinib (200 mg) (n = 299) | Placebo (n = 278) |
|---|---|---|
| Total adverse events (AEs) | 507 | 431 |
| Investigator-reported events in >5% of fenebrutinib-treated patients in RCTs | | |
| Nasopharyngitis | 18 (6.0%) | 13 (4.7%) |
| Nausea | 17 (5.7%) | 12 (4.3%) |
| Headache | 16 (5.4%) | 17 (6.1%) |
| Number of patients with | | |
| Fatal AE* | 1 (0.3%) | 2 (0.7%) |
| Serious AE | 18 (6.0%) | 9 (3.2%) |
| Serious AE related to blinded fenebrutinib | 6 (2.0%) | 5 (1.8%) |
| Study withdrawal due to AE | 17 (5.7%) | 13 (4.7%) |
| AE leading to treatment withdrawal | 32 (10.7%) | 13 (4.7%) |

*The cause of death of the patient in the fenebrutinib arm was acute myocardial infarction, deemed unrelated to fenebrutinib.
RCT: Randomized clinical trial.

Table 7 summarizes the percent of patients with infection adverse events in the previous randomized clinical trials. There was no imbalance of infection rates in fenebrutinib arms compared to placebo (standard of care for each condition), despite background immunosuppressant therapy use in RA and SLE (for example, methotrexate, corticosteroids). There was no imbalance in pattern, duration, seriousness, or severity of infections. Six patients (2.0%) had serious infections in the combined fenebrutinib arms, 5 patients (1.8%) in the combined placebo arms.

TABLE 7

Percent of patients with infection adverse events.

| | Fenebrutinib (200 mg) | Placebo | Median follow-up time |
|---|---|---|---|
| RA cohort 1 | 10.9% (n = 110) | 14.5% (n = 110) | 84 days |
| RA cohort 2 | 6.1% (n = 49) | 14.2% (n = 49) | 84 days |
| SLE | 46.6% (n = 88) | 51.2% (n = 84) | 336 days |
| CSU | 32.7% (n = 52) | 25.7% (n = 35) | 56 days |

Other potential class effects may be less relevant to fenebrutinib, possibly because of its increased selectivity for BTK. For example, bleeding or bruising was observed in 7.7% of patients in the fenebrutinib arms (n=23), and 3.2% in combined placebo arms (n=9). These rates are substantially lower than reports of ibrutinib-treated patients with B cell malignancies (bleeding or bruising, 39%; major hemorrhage, 4%; Imbruvica USPI, December 2020, <https://imbruvica.com/files/prescribing-information.pdf>). No fenebrutinib randomized clinical trial patients had atrial fibrillations, flutters, or other supraventricular tachyarrhythmias, which is substantially lower than what is reported for ibrutinib (4% Grade≥3 atrial fibrillation/flutter; 1% ventricular tachyarrhythmias; medium treatment time 19.1).

What is claimed is:

1. A method of treating relapsing multiple sclerosis (RMS) in a subject in need thereof, comprising administering to the subject about 200 mg fenebrutinib twice daily, or an equivalent amount of a pharmaceutically acceptable salt thereof.

2. The method of claim 1, wherein the subject's score on the Multiple Sclerosis Impact Scale-29 (MSIS-29) is improved.

3. The method of claim 1, comprising evaluating the subject using the Symbol Digit Modalities Test (SDMT).

4. The method of claim 1, wherein the free form of fenebrutinib is administered orally as one or more tablets or capsules.

5. The method of claim 1, wherein the subject:

is not concomitantly administered a strong CYP3A4 inhibitor; or is not concomitantly administered a strong CYP3A4 inducer; or is not concomitantly administered a moderate CYP3A4 inducer; or is not concomitantly administered a CYP3A4 substrate with a narrow therapeutic window;

or any combination thereof, while being administered about 200 mg fenebrutinib twice per day, or an equivalent amount of a pharmaceutically acceptable salt thereof.

6. A method of reducing the Annualized Relapse Rate (ARR) in a subject with RMS in need thereof, the method comprising administering to the subject about 200 mg fenebrutinib twice per day, or an equivalent amount of a pharmaceutically acceptable salt thereof.

7. The method of claim 6, wherein relapse comprises the subject experiencing a new or worsening neurological MS symptom, wherein the symptom persists for at least 24 hours, and wherein prior to experiencing the symptom the subject had a relatively stable or improving neurological state for at least 30 days.

8. The method of claim 7, wherein relapse comprises an increase of at least one of the following:

increase of half a step (0.5 point) on the Expanded Disability Status Scale (EDSS);

increase of two points on one functional systems score (FSS) selected from the group consisting of pyramidal, ambulation, cerebellar, brainstem, sensory, and visual; or increase of one point on two or more of FSS selected from the group consisting of pyramidal, ambulation, cerebellar, brainstem, sensory, and visual.

9. The method of claim 6, wherein the reduction of annualized relapse rate is greater than 25%.

10. The method of claim 6, wherein the free form of fenebrutinib is administered orally as one or more tablets or capsules.

11. The method of claim 6, wherein the subject:

is not concomitantly administered a strong CYP3A4 inhibitor; or is not concomitantly administered a strong CYP3A4 inducer; or is not concomitantly administered a moderate CYP3A4 inducer; or is not concomitantly administered a CYP3A4 substrate with a narrow therapeutic window;

or any combination thereof, while being administered about 200 mg fenebrutinib twice per day, or an equivalent amount of a pharmaceutically acceptable salt thereof.

12. A method of:

increasing time to onset of composite 12-week disability progression (cCDP12) in a subject with RMS in need thereof; or increasing time to onset of 12-week confirmed disability progression (CDP12) in a subject with RMS in need thereof, or reducing the risk of experiencing cCDP12 in a subject with RMS in need thereof; or increasing time to onset of composite 24-week confirmed disability progression (cCDP24) in a subject with RMS in need thereof; or increasing time to onset of 24-week confirmed disability progression (CDP24) in a subject with RMS in need thereof; or reducing the risk of experiencing cCDP24 in a subject with RMS in need thereof;

each method of comprising administering to the subject about 200 mg fenebrutinib twice daily, or an equivalent amount of a pharmaceutically acceptable salt thereof.

13. The method of claim 12, wherein the method is of increasing time to onset of cCDP12 in a subject with RMS in need thereof.

14. The method of claim 13, wherein onset of cCDP12 comprises at least one of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; or (c) increase form baseline of at least 20% in T25FWT;

and wherein the change from baseline is confirmed at least 12 weeks after the initial increase.

15. The method of claim 12, wherein the method is increasing time to onset of cCDP24 in a subject with RMS in need thereof.

16. The method of claim 15, wherein onset of cCDP24 comprises at least one of:

(a) an increase from baseline in EDSS score of at least 1.0 point in a subject with a baseline EDSS score of less than or equal to 5.5; or an increase from baseline in EDSS score of at least 0.5 point in a subject with a baseline EDSS score of greater than 5.5 points;

(b) increase from baseline of at least 20% in time to complete the 9-HPT; or (b) increase from baseline of at least 20% in T25FWT;

and wherein the change from baseline is confirmed at least 24 weeks after the initial increase.

17. The method of claim 12, wherein the free form of fenebrutinib is administered orally as one or more tablets or capsules.

* * * * *